(12) United States Patent
Lappi et al.

(10) Patent No.: US 11,530,243 B2
(45) Date of Patent: Dec. 20, 2022

(54) NON-CLEAVABLE SUBSTANCE P CONJUGATES AND METHODS OF USE THEREOF

(71) Applicant: VEIOVE ANIMAL HEALTH INC., San Diego, CA (US)

(72) Inventors: Douglas A Lappi, San Diego, CA (US); Brian J Russell, San Diego, CA (US); E Denise Higgins, San Diego, CA (US)

(73) Assignee: VEIOVE ANIMAL HEALTH INC., San Diego, CA (US)

( * ) Notice: Subject to any disclaimer, the term of this patent is extended or adjusted under 35 U.S.C. 154(b) by 0 days.

(21) Appl. No.: 15/047,193

(22) Filed: Feb. 18, 2016

(65) Prior Publication Data
US 2017/0267724 A1 Sep. 21, 2017

(51) Int. Cl.
| | |
|---|---|
| C07K 7/22 | (2006.01) |
| C07K 14/415 | (2006.01) |
| C07K 14/00 | (2006.01) |
| C12N 9/52 | (2006.01) |
| A61K 47/64 | (2017.01) |
| A61K 38/00 | (2006.01) |

(52) U.S. Cl.
CPC ............... *C07K 7/22* (2013.01); *A61K 47/64* (2017.08); *A61K 47/6415* (2017.08); *C07K 14/00* (2013.01); *C07K 14/415* (2013.01); *C12N 9/52* (2013.01); *C12Y 304/24069* (2013.01); *A61K 38/00* (2013.01); *C07K 2319/55* (2013.01)

(58) Field of Classification Search
None
See application file for complete search history.

(56) References Cited

U.S. PATENT DOCUMENTS

| 6,063,758 A | 5/2000 | Lappi et al. | |
|---|---|---|---|
| 7,741,435 B2 * | 6/2010 | Lappi | C07K 7/22 530/326 |
| 2011/0288011 A1 * | 11/2011 | Castaigne | A61K 47/48246 514/5.3 |

FOREIGN PATENT DOCUMENTS

EP 1623994 A2 * 2/2006 ............. C07K 14/00

OTHER PUBLICATIONS

Bastings, M.M.C. et al. 2008. One-step refolding and purification of disulfide-containing proteins with a C-terminal MESNA thioester. BMC Biotechnology 8(76): 1-7. specif. p. 1.*
Trivedi, M.V. et al. 2009. The role of thiols and disulfides on protein stability. Current Protein and Peptide Science 10: 614-625. specif. pp. 7, 8, 20.*
Benatti, L. et al. 1989. Nucleotide sequence of cDNA coding for saporin-6, a type-1 ribosome-inactivating protein from Saponaria officinalis. European Journal of Biochemistry 183: 465-470. specif. p. 469.*
Schottelius, M. et al. 2015. An optimized strategy for the mild and efficient solution phase iodination of tyrosine residues in bioactive peptides. Tetrahedron Letters 56: 6602-6605. specif. pp. 6602, 6605.*
Chen, X. et al. 2013. Fusion protein linkers: property, design and functionality. Advanced Drug Delivery Reviews 65: 1357-1369. specif. pp. 1359, 1360.*
Akiyama, T. et al. 2015. A central role for spinal dorsal horn neurons that express neurokinin-1 receptors in chronic itch. PAIN 156: 1240-1245; specif. p. 1240.*
Almay et al., Substance P in CSF of patients with chronic pain syndromes. Pain 33(1):3-9 (1988).
Amlot et al., A phase I study of an anti-CD22-deglycosylated ricin A chain immunotoxin in the treatment of B-cell lymphomas resistant to conventional therapy. Blood 82(9):2624-33 (1993).
Basbaum., Spinal mechanisms of acute and persistent pain. Reg Anesth Pain Med 24(1):59-67 (1999).
Behar-Cohen et al., In vivo inhibition of lens regrowth by fibroblast growth factor 2-saporin. Invest Ophthalmol Vis Sci 36(12):2434-48 (1995).
Blasi et al., Botulinum neurotoxin A selectively cleaves the synaptic protein SNAP-25. Nature 365(6442): 160-3 (1993).
Bonham., Neurotransmitters in the CNS control of breathing. Respir Physiol 101 (3):219-30 (1995).
Brin et al., Safety and efficacy of NeuroBloc (botulinum toxin type B) in type A-resistant cervical dystonia. Neurology 53(7):1431-8 (1999).
Brown et al., Intrathecal substance P-saporin in the dog: efficacy in bone cancer pain. Anesthesiology 119(5):1178-85 (2013).
Cava et al., N-Phenylmaleimide. Organic Syntheses 41:93 (1961).
Cesaro et al. Pain and its treatments. Eur Neurol 38(3):209-15 (1997).
Choi et al., Carrageenan induced phosphorylation of Akt is dependent on neurokinin-1 expressing neurons in the superficial dorsal horn. Mol Pain 8:4 (2012).
Ebner et al., The role of substance P in stress and anxiety responses. Amino Acids 31(3):251-72 (2006).
Falini et al., Response of refractory Hodgkin's disease to monoclonal anti-CD30 immunotoxin. Lancet 339(8803):1195-6 (1992).
Foran et al., Evaluation of the therapeutic usefulness of botulinum neurotoxin B, C1, E, and F compared with the long lasting type A. Basis for distinct durations of inhibition of exocytosis in central neurons. J Biol Chem 278(2):1363-71 (2003).

(Continued)

*Primary Examiner* — Olivia M. Wise
*Assistant Examiner* — Sharon M. Papciak
(74) *Attorney, Agent, or Firm* — Wilson Sonsini Goodrich & Rosati

(57) ABSTRACT

Described herein are methods for treating disorders that relate to neurons that express the neurokinin-1 receptor (NK-1R) in a subject which comprises administering to the subject an effective amount of the pharmaceutical composition of the non-cleavable conjugate comprising a molecule that is recognized and internalized by the NK-1R, and a molecule that is taken inside the cell to kill or temporarily alter the cell.

4 Claims, 11 Drawing Sheets

Specification includes a Sequence Listing.

(56) References Cited

OTHER PUBLICATIONS

Frankel et al., Anti-CD3 recombinant diphtheria immunotoxin therapy of cutaneous T cell lymphoma. Curr Drug Targets 10(2):104-9 (2009).

Herrera et al., A phase 1 study of Combotox in pediatric patients with refractory B-lineage acute lymphoblastic leukemia. J Pediatr Hematol Oncol 31(12):936-41 (2009).

Huston et al., Sequence-specific effects of neurokinin substance P on memory, reinforcement, and brain dopamine activity. Psychopharmacology (Berl) 112(2-3): 147-62 (1993).

Katayama et al., Solution behavior of a novel biopharmaceutical drug candidate: a gonadotropin-toxin conjugate. Drug Dev Ind Pharm 32(10):1175-84 (2006).

Khasabov et al., Spinal neurons that possess the substance P receptor are required for the development of central sensitization. J Neurosci 22(20):9086-98 (2002).

Lamanna et al., The Purification and Crystallization of Clostridium botulinum Type A Toxin. Science 103(2681):613-4 (1946).

Lambert et al., Purified immunotoxins that are reactive with human lymphoid cells. Monoclonal antibodies conjugated to the ribosome-inactivating proteins gelonin and the pokeweed antiviral proteins. J Biol Chem 260(22):12035-41 (1985).

Lappi et al., Biological and chemical characterization of basic FGF-saporin mitotoxin. Biochemical and biophysical research communications 160(2):917-923 (1989).

Lyu et al., The rGel/BLyS fusion toxin inhibits diffuse large 8-cell lymphoma growth in vitro and in vivo. Neoplasia 12(5):366-75 (2010).

Mantyh et al., Inhibition of hyperalgesia by ablation of lamina I spinal neurons expressing the substance P receptor. Science 278(5336):275-9 (1997).

Martin et al. Focal inhibitory interneuron loss and principal cell hyperexcitability in the rat hippocampus after microinjection of a neurotoxic conjugate of saporin and a peptidase-resistant analog of Substance P. J Comp Neurol 436(2):127-52 (2001).

Masuho et al., Importance of the antigen-binding valency and the nature of the cross-linking bond in ricin A-chain conjugates with antibody. J Biochem 91 (5):1583-91 (1982).

Matsumura et al., Characterization of the hyperalgesic effect induced by intrathecal injection of substance P. Neuropharmacology 24(5):421-6 (1985).

Meeus et al., Central sensitization: a biopsychosocial explanation for chronic widespread pain in patients with fibromyalgia and chronic fatigue syndrome. Clin Rheumatol 26(4):465-73 (2007).

Meini et al., Tachykinin control of ferret airways: mucus secretion, bronchoconstriction and receptor mapping. Neuropeptides 24(2):81-9 (1993).

Moeller-Bertram et al., Evidence for acute central sensitization to prolonged experimental pain in posttraumatic stress disorder. Pain Med 15(5):762-71 (2014).

Montecucco et al., Tetanus and botulism neurotoxins: a new group of zinc proteases. Trends Biochem Sci 18(9):324-7 (1993).

Nagy. Kinetics and mechanisms of thiol-disulfide exchange covering direct substitution and thiol oxidation-mediated pathways. Antioxid. Redox Signal. 18:1623-41 (2013).

Nichols et al., Transmission of chronic nociception by spinal neurons expressing the substance P receptor. Science 286(5444):1558-61 (1999).

Pergolizzi et al., Treatment Considerations for Cancer Pain: A Global Perspective. Pain Pract 15(8):778-792 (2015).

Polito et al., Immunotoxins and other conjugates containing saporin-56 for cancer therapy. Toxins (Basel) 3(6):697-720 (2011).

Rajashekhar et al., Design of biologically active peptides with non-peptidic structural elements. Biological and physical properties of a synthetic analogue of beta-endorphin with unnatural amino acids in the region 6-12. J Biol Chem 261 (29):13617-23 (1986).

Ranoux et al., Botulinum toxin type A induces direct analgesic effects in chronic neuropathic pain. Ann Neurol 64(3):274-83 (2008).

Sakurada et al., Behavioral activation of neurokinin-1 agonists in relation to enzymatic degradation in the spinal cord. J Pharm Sci 83(1):2-4 (1994).

Schnell et al., Clinical evaluation of ricin A-chain immunotoxins in patients with Hodgkin's lymphoma. Ann Oncol 14(5):729-36 (2003).

Seybold., The role of peptides in central sensitization. Handb Exp Pharmacol 194:451-91 (2009).

Stirpe., Ribosome-inactivating proteins: from toxins to useful proteins. Toxicon 67:12-6 (2013).

Suzuki et al., Superficial NK1-expressing neurons control spinal excitability through activation of descending pathways. Nat Neurosci 5(12):1319-26 (2002).

Thorpe et al., Toxicity of diphtheria toxin for lymphoblastoid cells is increased by conjugation to antilymphocytic globulin. Nature 271(5647):752-5 (1978).

Tousignant et al., Comparison of binding assay and biological activity on a NK-1 system with new selective agonists. Neuropeptides 14(4):275-83 (1989).

Van De Pavert et al., Effects of vasopressin and elimination of corticotropin-releasing hormone-target cells on pro-opiomelanocortin mRNA levels and adrenocorticotropin secretion in ovine anterior pituitary cells. J Endocrinol 154(1):139-47 (1997).

Vitetta et al., Phase I immunotoxin trial in patients with B-cell lymphoma. Cancer Res. 51(15):4052-8 (1991).

Weaver et al., Transferrin receptor ligand-targeted toxin conjugate (Tf-CRM107) for therapy of malignant gliomas. J Neurooncol 65(1):3-13 (2003).

Weisshaar et al., Ablating spinal NK1-bearing neurons eliminates the development of pain and reduces spinal neuronal hyperexcitability and inflammation from mechanical joint injury in the rat. J Pain 15(4): 378-86 (2014).

Wild et al., VEGF-DT385 toxin conjugate inhibits mammary adenocarcinoma development in a transgenic mouse model of spontaneous tumorigenesis. Breast Cancer Res Treat 85(2):161-71 (2004).

Wiley et al., Anti-nociceptive effects of selectively destroying substance P receptor-expressing dorsal horn neurons using (Sar9,Met(02)11]-substance P-saporin: behavioral and anatomical analyses. Neuroscience 146(3):1333-45 (2007).

Willis., Role of neurotransmitters in sensitization of pain responses. Ann N Y Acad Sci 933:142-56 (2001).

Woolf., Central sensitization: implications for the diagnosis and treatment of pain. Pain 152(3 Suppl):S2-15(2011).

\* cited by examiner

NON-CLEAVABLE SUBSTANCE P CONJUGATES AND METHODS OF USE THEREOF

SEQUENCE LISTING

The instant application contains a Sequence Listing which has been submitted in ASCII format via EFS-Web and is hereby incorporated by reference in its entirety. Said ASCII copy, created on May 5, 2017, is named 52445-701_201_SL.TXT and is 136 bytes in size.

TECHNICAL FIELD

This invention relates to a non-cleavable targeted conjugate that will bind to and enter cells expressing the neurokinin-1 receptor. More specifically, the invention relates to conjugates that do not undergo disulfide exchange and lose stability and activity, and use of said conjugates, to reduce or eliminate chronic pain and other neurokinin-1 receptor associated disorders.

Throughout this application, various publications may be referenced by Arabic numerals in parenthesis. Full citations for these publications may be found at the end of the Detailed Description of the Invention. The disclosures of all publications cited herein are in their entirety hereby incorporated by reference into this application to more fully describe the state of the art to which this invention pertains.

BACKGROUND OF THE INVENTION

The concept of directing a toxin to a specific population of cells as a therapeutic strategy was first published by Thorpe et al. in 1978 (1). Since that time, the field has grown greatly with several antibody-toxin conjugates reaching clinical trials (2-6). This strategy has been extended to the attachment of targeting molecules other than antibodies to various toxins, and the conjugates have been used in a wide range of research. Other targeting molecules have included proteins such as basic fibroblast growth factor (7, 8), vascular endothelial growth factor (9), and transferrin (10), as well as peptides such as gonadotrophin (11), and corticotrophin-releasing hormone (12).

The conjugation methods used to attach the functional molecules have not varied much. In part, this is because there are just a few practical protein chemical modification targets; primary amines, carboxyls, sulfhydryls, and carbonyls. As the toxin conjugate field grew, the most common conjugation techniques used disulfide chemistry to link two molecules. Early work done by Lambert et al. indicated that 2-iminothiolane modification of primary amines was the best method for preparing the ribosome-inactivating proteins gelonin and pokeweed antiviral protein for conjugation (13). Work done by Masuho et al. demonstrated that SPDP modification of sulfhydryl groups worked well with ricin (14).

One finding from both Masuho et al. and Lambert et al. is that the bond linking the targeting molecule (in both cases an antibody or antibody fragment) had to be cleavable for the toxin moiety to maintain activity. Masuho et al. compared conjugates created with 4 different linkers. The conjugate made with N-Succinimidyl 3-(2-pyridyldithio)-propionate (SPDP) displayed the highest activity. The two covalently linked conjugates, which used N,N'-o-phenylenedimaleimide and N-succinimidyl m-(N-maleimido)benzoate had very low cytotoxic activity. Another cleavable linker, a disulfide chain prepared with Ellman's reagent, was active, but with a lower $EC_{50}$ than the SPDP-linked conjugate. These data indicated that a non-disulfide containing construct would be less active.

The 2-iminothiolane treated gelonin and pokeweed antiviral protein used in Lambert et al. was conjugated using either a cleavable SPDP linkage, or a non-cleavable succinimidyl-4-(N-maleimidomethyl)cyclohexane-1-carboxylate (SMCC) linkage. The results indicate that the cytotoxic activity of a covalently linked antibody-toxin conjugate was reduced by about 70% from that of a conjugate made with a cleavable linker.

The takeaway lesson in the field was that ribosome-inactivating protein conjugates must be made with cleavable linkers in order to maintain cytotoxic activity.

One of the most common ribosome-inactivating proteins used from basic research to the clinic is saporin, isolated from the plant Saponaria officinalis, or soapwort. Saporin has no targeting mechanism of its own; therefore non-specific cell killing is kept at a minimum. In order for saporin to kill non-targeted cells it must be present at very high concentrations. The various ribosome-inactivating proteins use enzymatic methods to destroy cellular ribosomes, irreversibly inactivating protein synthesis (15). Ribosome-inactivating proteins have been researched extensively as cancer therapeutics (16-18). A cleavable conjugate of the peptide substance P and saporin (SP-SAP) has been used to treat chronic pain in laboratory animals (19).

Substance P (SP) is an 11-amino acid peptide that plays roles in a number of different systems. The receptor for this peptide is NK-1R. SP and the NK-1R have been shown to be involved with respiratory rhythm (20), mood disorders, anxiety and stress (21), and reinforcement (22). One of the most important roles for SP is in the spinal cord in the transmission of pain signals from peripheral pain receptors to the brain (23-25). Work in the 1980's began to implicate the SP/NK-1R system in the establishment and maintenance of a chronic pain state (19, 26). As this work progressed it became clear that NK-1R-expressing neurons in the spinal cord were responsible for transmission of the chronic pain signal (24, 27, 28).

In 1997 Mantyh et al. utilized a conjugate of SP and the ribosome-inactivating protein saporin to eliminate chronic pain in rats (19). This conjugate used an N-terminal extended version of SP. The peptide extension contained a glycine spacer and an N-terminal cysteine for conjugation. The modified SP was conjugated to derivatized saporin using a cleavable SPDP linker. This conjugate is described in U.S. Pat. No. 6,063,758 (29) and has been used extensively to investigate chronic pain (30, 31).

In 2001 Martin and Sloviter made the first investigation using a conjugate in which the SP moiety was a peptidase resistant analog of SP called stable substance P (SSP) (32). SSP contains two amino acid substitutions from the native sequence. The glycine at position 9 has been replaced with sarcosine, and the methionine at position 11 is oxidized (33). Not only was this peptide found to be highly selective for the NK-1R over the NK-2R and NK-3R (34), it was found to be much more active than native SP (33), in large part because of its resistance to peptidase digestion (35).

Internalization of a toxin such as a ribosome-inactivating protein will kill the cell. The various ribosome-inactivating proteins use enzymatic methods to destroy cellular ribosomes, thereby irreversibly inactivating protein synthesis (15). Use of a toxin such as a ribosome-inactivating protein will eliminate the cell, removing it completely. Ribosome-inactivating proteins have been researched extensively as cancer therapeutics (16-18). An example of a type-1 ribosome-inactivating protein is saporin, with a molecular weight of 30,000 daltons (17). The activity of saporin is, as the family name suggests, the inactivation of ribosomes, the 'workbench' for protein synthesis in a cell. This will cause protein synthesis to come to a halt, and result in the death of the cell (36). Saporin, unlike ricin, has no intrinsic method of cell-entry; the native protein is nontoxic until the cell is exposed to extremely high concentrations. Attaching a specific targeting molecule to saporin, or any other ribosome-inactivating protein, creates a cytotoxic agent that, when used at low concentrations, will eliminate very specific cell populations.

A conjugate of substance P and the type I ribosome-inactivating protein saporin has been used to in preclinical studies of chronic pain (19, 37). A conjugate of substance P and the type I ribosome-inactivating protein saporin has been used in a veterinary clinical trial (38). A conjugate of substance P and the type I ribosome-inactivating protein saporin has been used to in preclinical studies of chronic itch (39).

Central sensitization is a long-term potentiation of spinal cord neurons that creates a hyperexcitation state that is a characteristic of several maladies associated with pain and itch (40). SP-SAP has been reported by several authors to be able to prevent either maintenance or establishment of central sensitization (41-43). Because of this property, SP-SAP should be useful for the treatment of maladies such as chronic pain (40), fibromyalgia and chronic fatigue syndrome (44), post-traumatic stress disorder (45), and chronic itch (39), among other afflictions (46).

The primary example of a toxin that can prevent neurotransmission yet not kill the neuron is botulinum toxin. Purification of this toxin was first reported in 1946 (47), and the mechanism of action was deduced by various groups in the 1990's (48, 49). Botulinum toxins work by cleaving the synaptic vesicle protein SNAP25, preventing the formation of the vesicle (50). The vesicles are necessary to carry neurotransmitters to the ending of the axons, where they fuse with the plasma membrane and release the neurotransmitters into the synaptic cleft. If the vesicles do not form, neurotransmission cannot take place. Use of an analog of botulinum toxin will inactivate neurons for a period of 14 weeks for chronic pain (51), and 16 weeks for type-A resistant cervical dystonia (52).

The method of making local injections of conjugates that will only target specific cell populations is termed molecular neurosurgery. Molecular neurosurgery is a far more specific lesioning technique than administration of non-specific toxins, or physical techniques such as surgical removal of tissue, or electrolytic lesions. Molecular neurosurgery provides a method for elimination or temporary inactivation of specific cell populations, leaving non-targeted cells intact and fully functional. Martin and Sloviter (32) utilized this technique in the hippocampus to eliminate inhibitory neurons. Martin and Sloviter injected 0.4 ng of SSP-SAP, a toxin specific for neurons that express the substance P receptor (NK-1R), directly into the hippocampus. Cells expressing the NK-1R in the hippocampus were eliminated within a radius of 1-2 mm from the injection site. The specificity of the toxin conjugate was confirmed by the concurrent elimination of markers co-expressed by NK-1R-expressing neurons such as parvalbumin, cholecystokinin, somatostatin, calbindin, and calretinin. Other hippocampal cells such as the NK-1R-negative dentate granule cells, hilar mossy cells, and CA1-CA3 pyramidal cells were left intact and unharmed.

SPECIFICATION

Summary of the Invention

This invention provides noncleavable conjugates and methods for treating neurokinin-1 receptor (NK-1R)-related disorders comprising a molecule that is recognized and internalized by cells expressing the NK-1R, and a molecule that is taken inside the cell to kill or temporarily alter the cell.

This invention provides a method of reducing chronic pain in a subject comprising administering to the subject an effective amount of the improved pharmaceutical composition of a noncleavable conjugate comprising a molecule that binds the NK-1R, and analogs thereof, and a molecule that kills or temporarily alters a cell, so as to reduce chronic pain in a subject.

This invention provides a method of selectively killing or temporarily altering NK-1R-expressing cells in a subject comprising administering to the subject an effective amount of the noncleavable conjugate comprising a molecule that binds the NK-1R, and analogs thereof, and a molecule that kills or temporarily alters a cell, so as to selectively destroy or inactivate NK-1R-expressing cells.

Lastly, this invention provides a method for treating an NK-1R-associated disorder in a subject, which comprises administering to the subject an amount of the improved pharmaceutical composition comprising a molecule that binds the NK-1R, and analogs thereof, and a molecule that kills or temporarily alters a cell, so as to reduce symptoms in a subject thereby treating a disorder associated with the NK-1R.

DETAILED DESCRIPTION OF THE INVENTION

Figure 1:
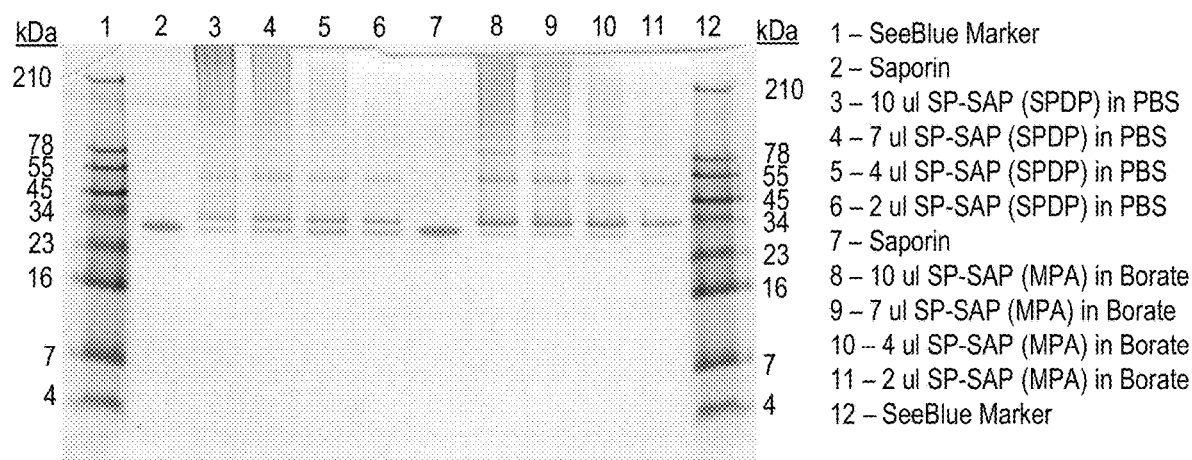
FIG. 1 shows coomassie-stained SDS-PAGE of cleavable SP-SAP.

This invention provides a non-cleavable conjugate comprising Substance P and Saporin (SP-SAP). In one embodiment the conjugate comprises an analog of Substance P. In another embodiment the conjugate comprises an analog of Saporin.

This invention provides a non-cleavable conjugate comprising a Substance P analog having the amino acid sequence (MPA)GGGGGGRPKPQQFFSarLMet(O.sub.2)-amide (SEQ ID No. 1) and a protein that is taken inside the cell to kill or temporarily alter the cell.

This invention provides a non-cleavable conjugate comprising a Substance P analog having the amino acid sequence (MPA)GGGGGGRPKPQQFFGLM-amide (SEQ ID No. 2), and a protein that is taken inside the cell to kill or temporarily alter the cell.

This invention provides a non-cleavable conjugate that contains a non-peptidic sequence such as (MPA)amino-ethoxy-ethoxy acetic acid (AEEAc) attached to Substance P or an analog thereof and a protein that is taken inside the cell to kill or temporarily alter the cell.

This invention provides a non-cleavable conjugate that contains an alkyne attached to a molecule that binds to the neurokinin-1 receptor and a protein that is taken inside the cell to kill or temporarily alter the cell.

This invention provides a non-cleavable conjugate that contains an azide attached to a molecule that binds to the neurokinin-1 receptor and a protein that is taken inside the cell to kill or temporarily alter the cell.

In one embodiment the non-cleavable conjugate comprises a peptide conjugated to a molecule that is taken inside the cell to kill or temporarily alter the cell. The peptide includes but is not limited to substance P, and analogs and fragments thereof.

In one embodiment the non-cleavable conjugate comprises an antibody or fragment thereof conjugated to a molecule that is taken inside the cell to kill or temporarily alter the cell.

Antibodies or antibody fragments that would be useful would be antibodies to the NK-1R. Antibody fragments useful in the present invention include F(ab')2, F(ab)2, Fab', Fab, Fv and the like including hybrid fragments. Preferred fragments are Fab', F(ab')2, Fab, and F(ab)2. Also useful are any subfragments retaining the hypervariable, antigen-binding region of an immunoglobulin and having a size similar to or smaller than a Fab' fragment. This will include genetically engineered and/or recombinant proteins, whether single-chain or multiple-chain, that incorporate an antigen-binding site and otherwise function in vivo as targeting vehicles in substantially the same way as natural immunoglobulin fragments. Fab' antibody fragments may be conveniently made by reductive cleavage of F(ab')2 fragments, which themselves may be made by pepsin digestion of intact immunoglobulin. Fab antibody fragments may be made by papain digestion of intact immunoglobulin, under reducing conditions, or by cleavage of F(ab)2 fragments which result from careful papain digestion of whole immunoglobulin. The fragments may also be produced by genetic engineering.

In one embodiment the non-cleavable conjugate comprises a molecule that binds to the neurokinin-1 receptor conjugated to a toxin. The toxin includes but is not limited to diphtheria toxin A, Pseudomonas aeruginosa exotoxin A, a maytansinoid, auristatin, or botulinum toxin and analogs and fragments thereof.

In one embodiment the non-cleavable conjugate comprises a molecule that binds to the neurokinin-1 receptor conjugated to a ribosome inactivating protein. The ribosome inactivating protein includes but is not limited to saporin, ricin A-chain, gelonin, pokeweed antiviral protein, and analogs and fragments thereof.

In one embodiment the non-cleavable conjugate comprises a peptide conjugated to a toxin. The peptide includes but is not limited to substance P and analogs and fragments thereof.

In one embodiment the non-cleavable conjugate comprises a protein or analog thereof that binds cells expressing the neurokinin-1 receptor conjugated to a toxin. The toxin includes but is not limited to diphtheria toxin A, Pseudomonas aeruginosa exotoxin A, a maytansinoid, an auristatin and analogs and fragments thereof.

In one embodiment the conjugate is manufactured using a peptide-based linker or spacer.

In one embodiment the conjugate is manufactured using a non-peptidic linker.

This invention provides a pharmaceutical composition comprising a therapeutically effective amount of a non-cleavable conjugate comprising Substance P or an analog thereof having an amino acid sequence of (MPA)GGGGG-GRPKPQQFFSarLMet(O.sub.2)-amide (SEQ ID No. 1) and a ribosome-inactivating protein and a pharmaceutically acceptable carrier. In one embodiment the ribosome-inactivating protein includes but is not limited to saporin, ricin A-chain, gelonin, pokeweed antiviral protein, and analogs and fragments thereof.

This invention provides a pharmaceutical composition comprising a therapeutically effective amount of a non-cleavable conjugate comprising Substance P or an analog thereof having an amino acid sequence of (MPA)GGGGG-GRPKPQQFFGLM-amide (SEQ ID No. 2) and a ribosome-inactivating protein and a pharmaceutically acceptable carrier. In one embodiment the ribosome-inactivating protein includes but is not limited to saporin, ricin A-chain, gelonin, pokeweed antiviral protein, and analogs and fragments thereof.

This invention provides a pharmaceutical composition comprising a therapeutically effective amount of a non-cleavable conjugate comprising a molecule that binds to the neurokinin-1 receptor and a protein that is taken inside the cell to kill or temporarily alter the cell and a pharmaceutically acceptable carrier.

This invention provides a pharmaceutical composition comprising a therapeutically effective amount of a non-cleavable conjugate comprising a molecule, with an attached alkyne, that binds to the neurokinin-1 receptor and a protein that is taken inside the cell to kill or temporarily alter the cell and a pharmaceutically acceptable carrier.

This invention provides a pharmaceutical composition comprising a therapeutically effective amount of a of a non-cleavable conjugate comprising a molecule, with an attached azide, that binds to the neurokinin-1 receptor and a protein that is taken inside the cell to kill or temporarily alter the cell and a pharmaceutically acceptable carrier.

This invention provides a method for treating the symptoms of chronic pain in a subject which comprises administering to the subject an effective amount of the pharmaceutical composition comprising a therapeutically effective amount of a non-cleavable conjugate comprising Substance P or an analog thereof having an amino acid sequence of (MPA)GGGGGGRPKPQQFFSarLMet(O.sub.2)-amide (SEQ ID No. 1) and a ribosome-inactivating protein and a pharmaceutically acceptable carrier. In one embodiment the ribosome-inactivating protein includes but is not limited to saporin, ricin A-chain, gelonin, pokeweed antiviral protein, and analogs and fragments thereof.

This invention provides a method for treating the symptoms of chronic pain in a subject which comprises administering to the subject an effective amount of the pharmaceutical composition comprising a therapeutically effective amount of a non-cleavable conjugate comprising Substance P or an analog thereof having an amino acid sequence of (MPA)GGGGGGRPKPQQFFGLM-amide (SEQ ID No. 2) and a ribosome-inactivating protein and a pharmaceutically acceptable carrier. In one embodiment the ribosome-inactivating protein includes but is not limited to saporin, ricin A-chain, gelonin, pokeweed antiviral protein, and analogs and fragments thereof.

This invention provides a method for treating the symptoms of chronic pain in a subject which comprises administering to the subject an effective amount of the pharmaceutical composition comprising a therapeutically effective amount of a non-cleavable conjugate comprising a molecule that binds to the neurokinin-1 receptor and a protein that is taken inside the cell to kill or temporarily alter the cell and a pharmaceutically acceptable carrier.

This invention provides a method for treating the symptoms of chronic pain in a subject which comprises administering to the subject an effective amount of the pharmaceutical composition comprising a therapeutically effective amount of a non-cleavable conjugate comprising a molecule, with an attached alkyne, that binds to the neurokinin-1 receptor and a protein that is taken inside the cell to kill or temporarily alter the cell and a pharmaceutically acceptable carrier.

This invention provides a method for treating the symptoms of chronic pain in a subject which comprises administering to the subject an effective amount of the pharmaceutical composition comprising a therapeutically effective amount of a non-cleavable conjugate comprising a molecule, with an attached azide, that binds to the neurokinin-1 receptor and a protein that is taken inside the cell to kill or temporarily alter the cell and a pharmaceutically acceptable carrier.

This invention provides a method for treating a neurokinin-1 receptor-associated disorder in a subject which comprises administering to the subject an effective amount of the pharmaceutical composition comprising a therapeutically effective amount of a non-cleavable conjugate comprising Substance P or an analog thereof having an amino acid sequence of (MPA)GGGGGGRPKPQQFFSarLMet(O.sub.2)-amide (SEQ ID No. 1) and a ribosome-inactivating protein and a pharmaceutically acceptable carrier. In one embodiment the ribosome-inactivating protein includes but is not limited to saporin, ricin A-chain, gelonin, pokeweed antiviral protein, and analogs and fragments thereof.

This invention provides a method for treating a neurokinin-1 receptor-associated disorder in a subject which comprises administering to the subject an effective amount of the pharmaceutical composition comprising a therapeutically effective amount of a non-cleavable conjugate comprising Substance P or an analog thereof having an amino acid sequence of (MPA)GGGGGGRPKPQQFFGLM-amide (SEQ ID No. 2) and a ribosome-inactivating protein and a pharmaceutically acceptable carrier. In one embodiment the ribosome-inactivating protein includes but is not limited to saporin, ricin A-chain, gelonin, pokeweed antiviral protein, and analogs and fragments thereof.

This invention provides a method for treating a neurokinin-1 receptor-associated disorder in a subject which comprises administering to the subject an effective amount of the pharmaceutical composition comprising a therapeutically effective amount of a non-cleavable conjugate comprising a molecule that binds to the neurokinin-1 receptor and a protein that is taken inside the cell to kill or temporarily alter the cell and a pharmaceutically acceptable carrier.

This invention provides a method for treating a neurokinin-1 receptor-associated disorder in a subject which comprises administering to the subject an effective amount of the pharmaceutical composition comprising a therapeutically effective amount of a non-cleavable conjugate comprising a molecule, with an attached alkyne, that binds to the neurokinin-1 receptor and a protein that is taken inside the cell to kill or temporarily alter the cell and a pharmaceutically acceptable carrier.

This invention provides a method for treating a neurokinin-1 receptor-associated disorder in a subject which comprises administering to the subject an effective amount of the pharmaceutical composition comprising a therapeutically effective amount of a non-cleavable conjugate comprising a molecule, with an attached azide, that binds to the neurokinin-1 receptor and a protein that is taken inside the cell to kill or temporarily alter the cell and a pharmaceutically acceptable carrier.

This invention provides a method for treating posttraumatic stress disorder (PTSD) in a subject which comprises administering to the subject an effective amount of the pharmaceutical composition comprising a therapeutically effective amount of a non-cleavable conjugate comprising Substance P or an analog thereof having an amino acid sequence of (MPA)GGGGGGRPKPQQFFSarLMet(O.sub.2)-amide (SEQ ID No. 1) and a ribosome-inactivating protein and a pharmaceutically acceptable carrier. In one embodiment the ribosome-inactivating protein includes but is not limited to saporin, ricin A-chain, gelonin, pokeweed antiviral protein, and analogs and fragments thereof.

This invention provides a method for treating posttraumatic stress disorder (PTSD) in a subject which comprises administering to the subject an effective amount of the pharmaceutical composition comprising a therapeutically effective amount of a non-cleavable conjugate comprising Substance P or an analog thereof having an amino acid sequence of (MPA)GGGGGGRPKPQQFFGLM-amide (SEQ ID No. 2) and a ribosome-inactivating protein and a pharmaceutically acceptable carrier. In one embodiment the ribosome-inactivating protein includes but is not limited to saporin, ricin A-chain, gelonin, pokeweed antiviral protein, and analogs and fragments thereof.

This invention provides a method for treating posttraumatic stress disorder (PTSD) in a subject which comprises administering to the subject an effective amount of the pharmaceutical composition comprising a therapeutically effective amount of a non-cleavable conjugate comprising a molecule that binds to the neurokinin-1 receptor and a protein that is taken inside the cell to kill or temporarily alter the cell and a pharmaceutically acceptable carrier.

This invention provides a method for treating posttraumatic stress disorder (PTSD) in a subject which comprises administering to the subject an effective amount of the pharmaceutical composition comprising a therapeutically effective amount of a non-cleavable conjugate comprising a molecule, with an attached alkyne, that binds to the neurokinin-1 receptor and a protein that is taken inside the cell to kill or temporarily alter the cell and a pharmaceutically acceptable carrier.

This invention provides a method for treating posttraumatic stress disorder (PTSD) in a subject which comprises administering to the subject an effective amount of the pharmaceutical composition comprising a therapeutically effective amount of a non-cleavable conjugate comprising a molecule, with an attached azide, that binds to the neurokinin-1 receptor and a protein that is taken inside the cell to kill or temporarily alter the cell and a pharmaceutically acceptable carrier.

This invention provides a method for treating the symptoms of itch in a subject which comprises administering to the subject an effective amount of the pharmaceutical composition comprising a therapeutically effective amount of a non-cleavable conjugate comprising Substance P or an analog thereof having an amino acid sequence of (MPA) GGGGGGRPKPQQFFSarLMet(O.sub.2)-amide (SEQ ID No. 1) and a ribosome-inactivating protein and a pharmaceutically acceptable carrier. In one embodiment the ribosome-inactivating protein includes but is not limited to saporin, ricin A-chain, gelonin, pokeweed antiviral protein, and analogs and fragments thereof.

This invention provides a method for treating the symptoms of itch in a subject which comprises administering to the subject an effective amount of the pharmaceutical composition comprising a therapeutically effective amount of a non-cleavable conjugate comprising Substance P or an analog thereof having an amino acid sequence of (MPA) GGGGGGRPKPQQFFGLM-amide (SEQ ID No. 2) and a ribosome-inactivating protein and a pharmaceutically acceptable carrier. In one embodiment the ribosome-inactivating protein includes but is not limited to saporin, ricin A-chain, gelonin, pokeweed antiviral protein, and analogs and fragments thereof.

This invention provides a method for treating the symptoms of itch in a subject which comprises administering to the subject an effective amount of the pharmaceutical composition comprising a therapeutically effective amount of a non-cleavable conjugate comprising a molecule that binds to the neurokinin-1 receptor and a protein that is taken inside the cell to kill or temporarily alter the cell and a pharmaceutically acceptable carrier.

This invention provides a method for treating the symptoms of itch in a subject which comprises administering to the subject an effective amount of the pharmaceutical composition comprising a therapeutically effective amount of a non-cleavable conjugate comprising a molecule, with an attached alkyne, that binds to the neurokinin-1 receptor and a protein that is taken inside the cell to kill or temporarily alter the cell and a pharmaceutically acceptable carrier.

This invention provides a method for treating the symptoms of itch in a subject which comprises administering to the subject an effective amount of the pharmaceutical composition comprising a therapeutically effective amount of a non-cleavable conjugate comprising a molecule, with an attached azide, that binds to the neurokinin-1 receptor and a protein that is taken inside the cell to kill or temporarily alter the cell and a pharmaceutically acceptable carrier.

This invention provides a method for treating diseases or disorders with symptoms of central sensitization in a subject which comprises administering to the subject an effective amount of the pharmaceutical composition comprising a therapeutically effective amount of a non-cleavable conjugate comprising Substance P or an analog thereof having an amino acid sequence of (MPA)GGGGGGRPKPQQFFSarL-Met(O.sub.2)-amide (SEQ ID No. 1) and a ribosome-inactivating protein and a pharmaceutically acceptable carrier. In one embodiment the ribosome-inactivating protein includes but is not limited to saporin, ricin A-chain, gelonin, pokeweed antiviral protein, and analogs and fragments thereof.

This invention provides a method for treating diseases or disorders with symptoms of central sensitization in a subject an effective amount of the pharmaceutical composition comprising a therapeutically effective amount of a non-cleavable conjugate comprising Substance P or an analog thereof having an amino acid sequence of (MPA)GGGGG-GRPKPQQFFGLM-amide (SEQ ID No. 2) and a ribosome-inactivating protein and a pharmaceutically acceptable carrier. In one embodiment the ribosome-inactivating protein includes but is not limited to saporin, ricin A-chain, gelonin, pokeweed antiviral protein, and analogs and fragments thereof.

This invention provides a method for treating diseases or disorders with symptoms of central sensitization in a subject an effective amount of the pharmaceutical composition comprising a therapeutically effective amount of a non-cleavable conjugate comprising a molecule that binds to the neurokinin-1 receptor and a protein that is taken inside the cell to kill or temporarily alter the cell and a pharmaceutically acceptable carrier.

This invention provides a method for treating diseases or disorders with symptoms of central sensitization in a subject an effective amount of the pharmaceutical composition comprising a therapeutically effective amount of a non-cleavable conjugate comprising a molecule, with an attached alkyne, that binds to the neurokinin-1 receptor and a protein that is taken inside the cell to kill or temporarily alter the cell and a pharmaceutically acceptable carrier.

This invention provides a method for treating diseases or disorders with symptoms of central sensitization in a subject an effective amount of the pharmaceutical composition comprising a therapeutically effective amount of a non-cleavable conjugate comprising a molecule, with an attached azide, that binds to the neurokinin-1 receptor and a protein that is taken inside the cell to kill or temporarily alter the cell and a pharmaceutically acceptable carrier.

Diseases or disorders with symptoms of itch include but are not limited to: respiratory conditions (e.g. asthma, allergic rhinitis), ophthalmic conditions (e.g. conjunctivitis), cutaneous conditions (e.g. allergic dermatitis, dermatitis by contact, psoriasis), intestinal conditions (e.g. ulcerative colitis, Crohn's disease), gastrointestinal tract, central nervous system disorders such as anxiety and psychosis, inflammatory diseases such as rheumatoid arthritis and inflammatory bowel diseases, as well as pain in any of the aforesaid conditions, including migraine.

Diseases or disorders with symptoms of central sensitization include but are not limited to: fibromyalgia, osteoarthritis, musculoskeletal disorders with generalized pain hypersensitivity (often called myofascial pain syndrome or "trigger points"), headache, temporomandibular joint disorders, dental pain, neuropathic pain, visceral pain hypersensitivity disorders, and post-surgical pain.

Other neurokinin-1 receptor related disorders or diseases include but are not limited to: Alzheimer's disease, multiple sclerosis, attenuation of morphine withdrawal, cardiovascular changes, oedema, such as oedema caused by thermal injury, chronic inflammatory diseases such as rheumatoid arthritis, asthma/bronchial hyperreactivity and other respiratory diseases including allergic rhinitis, inflammatory diseases of the gut including ulcerative colitis and Crohn's disease, ocular injury and ocular inflammatory diseases, proliferative vitreoretinopathy, irritable bowel syndrome and disorders of bladder function including cystitis and bladder detrusor hyperreflexia, demyelinating diseases such as multiple sclerosis and amyotrophic lateral sclerosis, asthmatic disease, small cell carcinomas, in particular small cell lung cancer, depression, dysthymic disorders, chronic obstructive airways disease, hypersensitivity disorders such as poison ivy, vasospastic diseases such as angina and Reynauld's disease, fibrosing and collagen diseases such as scleroderma and eosinophilic fascioliasis, reflex sympathetic dystrophy such as shoulder/hand syndrome, addiction disorders such as alcoholism, stress related somatic disorders, neuropathy, neuralgia, disorder related to immune enhancement or suppression such as systemic lupus erythmatosis conjunctivitis, vernal conjunctivitis, contact dermatitis, atopic dermatitis, urticaria, and other eczematoid dermatitis and emesis; central nervous system disorders such as anxiety, depression, psychosis and schizophrenia; neurodegenerative disorders such as AIDS related dementia, senile dementia of the Alzheimer type, Alzheimer's disease and Down's syndrome; demyelinating diseases such as multiple sclerosis (MS) and amyotrophic lateral sclerosis (ALS; Lou Gehrig's disease) and other neuropathological disorders such as peripheral neuropathy, inflammatory diseases such as inflammatory bowel disease, irritable bowel syndrome, psoriasis, fibrositis, ocular inflammation, osteoarthritis and rheumatoid arthritis; allergies such as eczema and rhinitis; hypersensitivity disorders such as poison ivy; ophthalmic diseases such as conjunctivitis, vernal conjunctivitis, dry eye syndrome, and the like; cutaneous diseases such as contact dermatitis, atopic dermatitis, urticaria, and other eczematoid dermatitis; oedema, such as oedema caused by thermal injury; addiction disorders such as alcoholism; stress related somatic disorders; reflex sympathetic dystrophy such as shoulder/hand syndrome; dysthymic disorders; neuropathy, such as diabetic or peripheral neuropathy and chemotherapy-induced nemopathy; postherpetic and other neuralgias; asthma; osteoarthritis; rheumatoid arthritis; dysesthesia; and especially migraine.

The subjects to be treated or whose tissue may be used herein may be a mammal, or more specifically a human, horse, pig, rabbit, dog, cat, monkey, or rodent. In the preferred embodiment the subject is a human.

The invention includes the pharmaceutically acceptable salts and complexes of all the compounds described herein. The salts include but are not limited to the following acids and bases. Examples of suitable inorganic acids include, but are not limited to, hydrochloric acid, hydrofluoric acid, hydrobromic acid, hydroiodic acid, sulfuric acid and boric acid. Examples of suitable organic acids include but are not limited to acetic acid, trifluoroacetic acid, formic acid, oxalic acid, malonic acid, succinic acid, tartaric acid, maleic acid, fumaric acid, methanesulfonic acid, trifluoromethanesulfonic acid, benzoic acid, glycolic acid, lactic acid, citric acid and mandelic acid. Examples of suitable inorganic bases include, but are not limited to, ammonia, hydroxyethylamine and hydrazine. Examples of suitable organic bases include, but are not limited to, methylamine, ethylamine, trimethylamine, triethylamine, ethylenediamine, hydroxyethylamine, morpholine, piperazine and guanidine. The invention further provides for the hydrates and polymorphs of all of the compounds described herein.

In one preferred embodiment, the pharmaceutical carrier may be a liquid and the pharmaceutical composition would be in the form of a solution. In another equally preferred embodiment, the pharmaceutically acceptable carrier is a solid and the pharmaceutical composition is in the form of a powder or tablet. In a further embodiment, the pharmaceutical carrier is a gel and the pharmaceutical composition is in the form of a suppository or cream. In a further embodiment, the compound may be formulated as part of a pharmaceutically acceptable transdermal patch.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for examples, calcium phosphate, magnesium stearate, talc, sugars, lactose, dextrin, starch, gelatin, cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both, or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric and polyhydric alcohols, e.g. glycols) and their derivatives, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellant, which are useful for intranasal administration.

Liquid pharmaceutical compositions which are sterile solutions or suspensions can be utilized for intramuscular, intrathecal, intratracheal, epidural, intraperitoneal or subcutaneous injections. Sterile solutions can also be administered intravenously. The compounds may be prepared as a sterile solid composition which may be dissolved or suspended at the time of administration using sterile water, saline, or other appropriate sterile injectable medium. Carriers are intended to include necessary and inert binders, suspending agents, lubricants, flavorants, sweeteners, preservatives, dyes and coatings. The compound can be administered orally in the form of a sterile solution or suspension containing other solutes or suspending agents, for example, enough saline or glucose to make the solution isotonic, bile salts, acacia, gelatin, sorbitan monoleate, polysorbate 80 (oleate esters of sorbitol and its anhydrides copolymerized with ethylene oxide) and the like.

The compound can also be administered orally either in liquid or solid composition form. Compositions suitable for oral administration include solid forms such as pills, capsules, granules, tablets and powders, and liquid forms such as solutions, syrups, elixirs and suspensions. Forms useful for parenteral administration include sterile solutions, emulsions and suspensions.

Examples of suitable pharmaceutical carriers include any of the standard pharmaceutically accepted carriers known to those of ordinary skill in the art. Examples of such pharmaceutical carriers include, but are not limited to, phosphate buffered saline solution, water, emulsions such as oil/water emulsions or a triglyceride emulsion, various types of wetting agents, tablets, coated tablets and capsules. A suitable pharmaceutically acceptable carrier may be selected taking into account the chosen mode of administration.

Besides containing an effective amount of the compounds described herein the pharmaceutical compositions may also include suitable diluents, preservatives, solubilizers, emulsifiers, adjuvant and/or carriers.

The resulting pharmaceutical compositions may be liquids or lyophilized or otherwise dried formulations. Examples of suitable diluents include, but are not limited to, Tris-HCL, Tris-acetate and Tris-phosphate. The diluents employed may vary in their buffer content, pH and/or ionic strength. Examples of representative additives which may be used in the present invention include, but are not limited to, albumin or gelatin to prevent absorption to surfaces, detergents (e.g., Tween 20, Tween 80, Pluronic F68, bile acid salts), solubilizing agents (e.g., Thimerosal, benzyl alcohol), bulking substances or tonicity modifiers (e.g., lactose, mannitol), covalent attachment of polymers such as polyethylene glycol to the protein, complexation with metal ions, or incorporation of the material into or onto particulate preparation of polymeric compounds such as polylactic acid, polyglycolic acid, polyvinyl pyrrolidone, etc. or into liposomes, microemulsions, micelles, unilamellar or multimellar vesicles, erythrocyte ghosts, or spheroplasts. Such compositions will influence the physical state, solubility, stability, rate of in vivo release, and rate of in vivo clearance of the compounds.

Examples of optional ingredients which may be included in the pharmaceutical compositions of the present invention include antioxidants, e.g., ascorbic acid; low molecular weight (less than about ten residues) polypeptides, i.e., polyarginine or tripeptide; proteins, such as serum albumin, gelatin, or immunoglobulins; amino acids, such as glycine, glutamine acid, aspartic acid, or arginine; chelating agents such as EDTA; and sugar alcohols such as mannitol or sorbitol.

The choice of composition will depend on the physical and chemical properties of the compounds. Controlled or sustained release compositions include formulation of lipohilic depots (e.g., fatty acids, waxes, oils). Also comprehended by the invention are particulate compositions coated with polymers (e.g., poloxamers or poloxamines) and compounds coupled to antibodies directed against tissue-specific receptors, ligands or antigens or coupled to ligands of tissue-specific receptors. Other embodiments of the compositions of the invention incorporate particulate forms of protective coatings, protease inhibitors or permeation enhancers for various routes of administration, including parenteral, pulmonary nasal and oral.

Suitable topical formulations include gels, creams, solutions, emulsions, carbohydrate polymers, biodegradable matrices thereof, vapors, mists, aerosols, or other inhalants. The compounds of the present invention may be encapsulated in a wafer, wax, film or solid carrier, including chewing gums. Permeation enhancers to aid in transport to movement across the epithelial layer are also known in the art and include, but are not limited to, dimethyl sulfoxide and glycols.

Optimal dosages to be administered may be determined by those skilled in the art, and will vary with the particular compound in use, the strength of the preparation, the mode of administration, and the advancement of the disease condition. Additional factors depending on the particular subject being treated, including subject age, weight, gender, diet, and time of administration, will result in a need to adjust dosages. Administration of the compound may be effected continuously or intermittently.

In any treatment regimen, the composition may be administered to a patient either singly or in a cocktail containing two or more targeted toxins, other therapeutic agents, compositions, or the like, including, but not limited to, immunosuppressive agents, tolerance-inducing agents, potentiators and side-effect relieving agents. Particularly preferred are immunosuppressive agents useful in suppressing allergic reactions of a host. Preferred immunosuppressive agents include prednisone, prednisolone, DECADRON (Merck, Sharp & Dohme, West Point, Pa.), cyclophosphamide, cyclosporine, 6-mercaptopurine, methotrexate, azathioprine and i.v. gamma globulin or their combination. Preferred potentiators include monensin, ammonium chloride, perhexiline, verapamil, amantadine and chloroquine. All of these agents are administered in generally-accepted efficacious dose ranges such as those disclosed in the Physician's Desk Reference, 41st Ed., Publisher Edward R. Barnhart, N.J. (1987).

In the treatment, an appropriate dosage level will generally be about 0.001 to 50 mg per kg patient body weight per day which can be administered in single or multiple doses. Preferably, the dosage level will be about 0.005 to about 25 mg/kg per day; more preferably about 0.01 to about 10 mg/kg per day; and even more preferably about 0.05 to about 1 mg/kg per day.

This invention is further illustrated in the Experimental Details Sections which follow. These sections are set forth to aid in understanding the invention but are not intended to, and should not be construed to, limit in any way the invention as set forth in the claims which follow thereafter.

Experimental Details Section

The invention describes the creation of a non-cleavable conjugate between substance P and its analogs, and saporin or other proteins. The novelty of these conjugates is the non-cleavable linker that does not reduce the activity of the conjugate.

When producing the Substance P-Saporin conjugate using the cleavable SPDP linker, it was found that there was a small amount of steady state disulfide exchange occurring in the final product (53). As a result, the conjugate final product contained a mixture of SP conjugated to saporin, saporin dimers, and presumably SP dimers (FIG. 1). FIG. 1: Coomassie stained NuPage gel of SP-SAP conjugated with a SPDP linker. The conjugate was dialyzed against PBS or borate buffered saline in order to examine whether either buffer could prevent disulfide exchange. Although less disulfide exchange occurred in the borate buffered saline, free $cys^{-1}$-SAP can be seen in SP-SAP from both buffers. The band with a molecular weight of approximately 60 kDa is dimerized $cys^{-1}$-SAP, also seen in both buffers.

Figure 2:
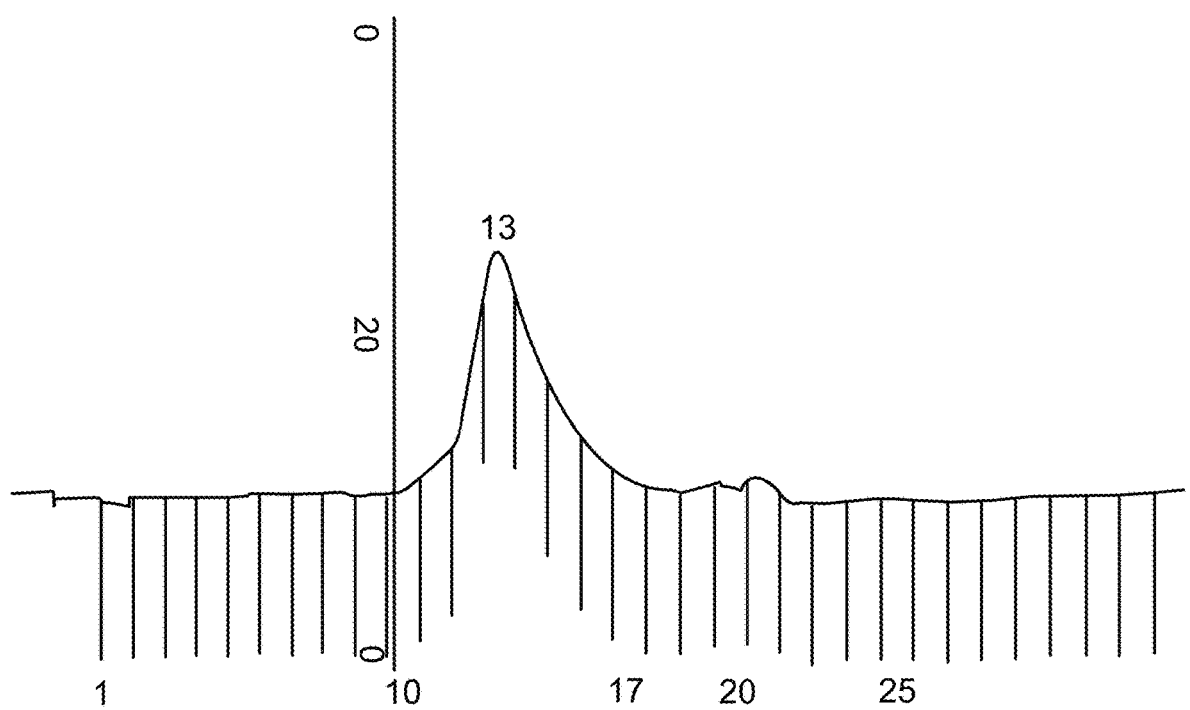
FIG. 2 shows the chromatogram of an S-100 column of cleavable SP-SAP.

A number of different methods to remove the impurities were examined, including ion-exchange chromatography and size-exclusion chromatography (FIG. 2). FIG. 2: Chromatogram of SP-SAP conjugated with a SPDP linker passed over a S-100 column. 1 ml of the conjugate was applied to a 17 ml S-100 column in 50 mM borate buffer pH 8.5. 1 ml fractions were collected. No observable separation of proteins was detected, and a coomassie stained gel of the fractions showed that free $cys^{-1}$-SAP was present along with the conjugate.

Given the tendency of the cleavable linker to assume an equilibrium in which a small amount of disulfide exchange occurs, none of these methods produced a homogeneous final product. This heterogeneous mixture was problematic for the advancement of SP-SAP as a therapeutic.

Despite evidence in peer-reviewed journals indicating that a non-cleavable linker was necessary to maintain cytotoxic activity, it was decided to utilize maleimide chemistry to create a conjugate. Maleimide is an unsaturated imide prepared from maleic anhydride by treatment with amines followed by dehydration (54). Maleimide-activated crosslinkers and labeling reagents react specifically with sulfhydryl groups at near neutral conditions (pH 6.5-7.5) to form stable thioether linkages. Disulfide bonds in protein structures (e.g., between cysteines) must be reduced to free thiols (sulfhydryls) to react with maleimide reagents. Extraneous thiols, such as most reducing agents, must be excluded from maleimide reaction buffers because they will compete for coupling sites. Short homobifunctional maleimide crosslinkers enable disulfide bridges in protein structures to be converted to permanent, irreducible linkages between cysteines. More commonly, the maleimide chemistry is used in combination with amine-reactive NHS-ester chemistry in the form of heterobifunctional crosslinkers that enable controlled, two-step conjugation of purified peptides and/or proteins.

As early as 1986 work was beginning on non-peptidic linkers (55). The advantages this kind of chemistry provides include reduced steric hindrance to improve binding, longer conjugate half life, and the ability to more easily modify the linker to fit specific needs.

The substance P used in the SP-SAP conjugate is synthesized commercially to contain a maleimidopropionic acid (MPA) group at the N-terminus of the peptide. In addition there is a spacer placed between the MPA group and the native peptide sequence, providing relief from any steric hindrance during receptor binding. The two modifications ensure that substance P will only be conjugated to saporin at a single known location that in no way affects the natural interaction of substance P with its receptor.

The saporin that is used in the SP-SAP conjugate is also modified. Rather than co-opting a potentially functional site necessary for the enzymatic activity, the saporin used in SP-SAP is recombinantly produced to contain an available, non-native cysteine at the amino terminus. As this is the only available cysteine within the saporin protein, there is only one location for the substance P and saporin to be linked. This conjugate has been designed at the amino acid level to ensure that every molecule of conjugate contains one substance P and one saporin, linked to each other at the designated, artificially introduced location.

Figure 3:
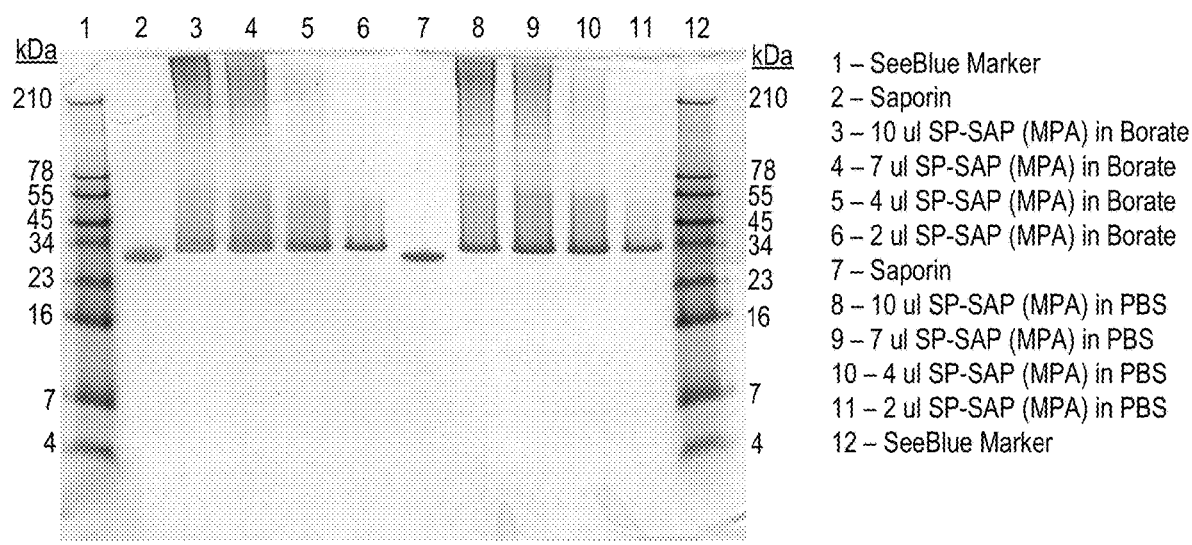
FIG. 3 shows coomassie-stained SDS-PAGE of non-cleavable SP-SAP.
Figure 4:
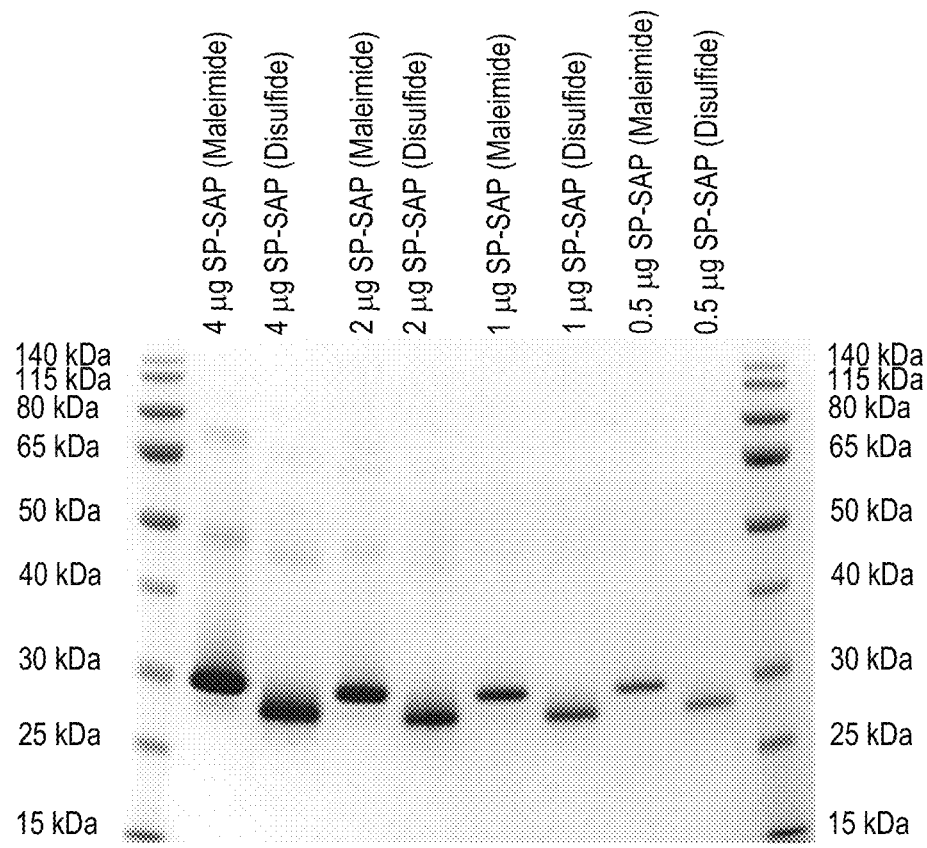
FIG. 4 shows coomassie-stained SDS-PAGE of non-cleavable (maleimide) and non-cleavable (disulfide) SP-SAP in the presence of reducing agent.
Figure 5:
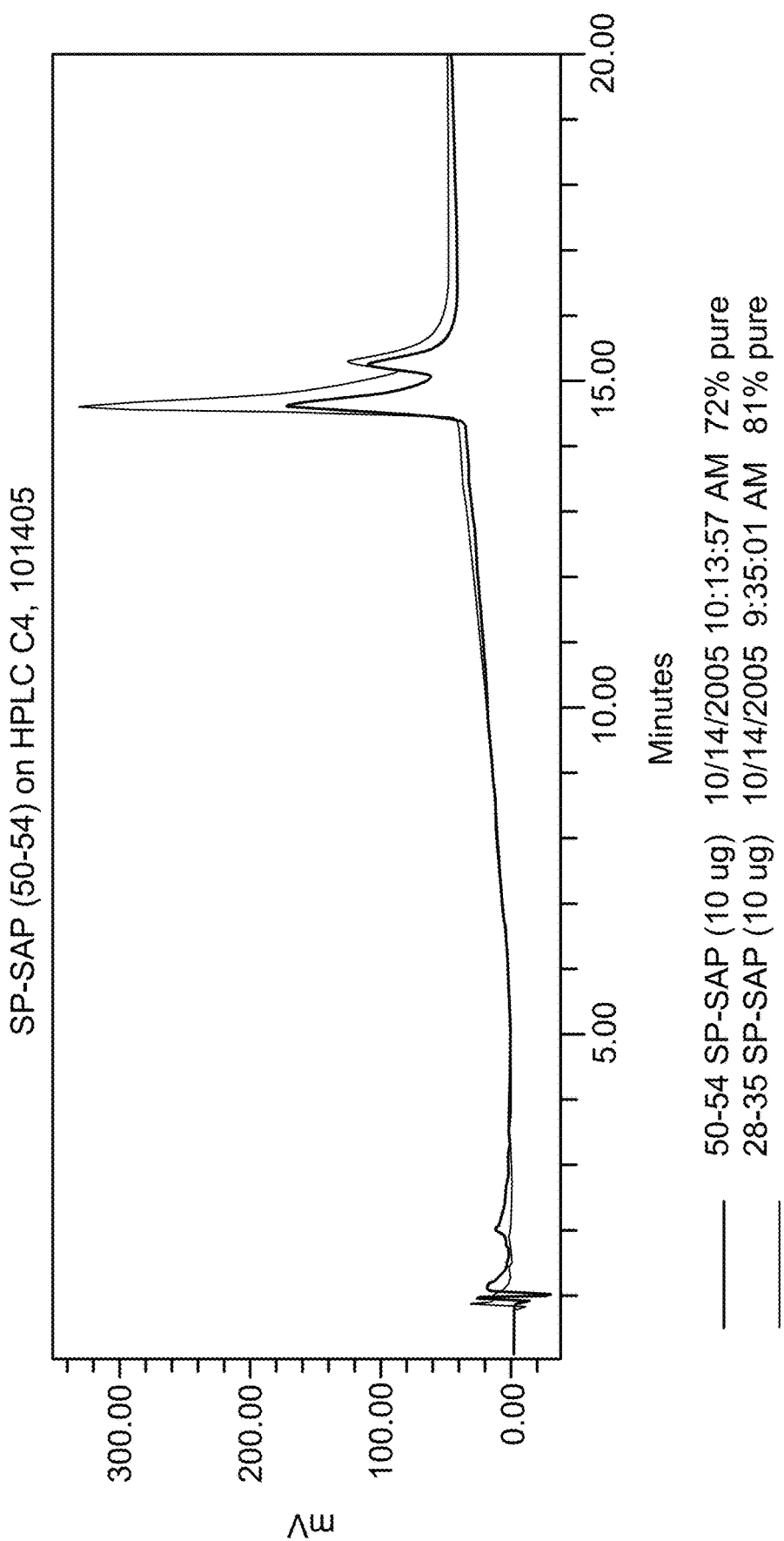
FIG. 5 shows HPLC of cleavable SP-SAP on a C4 column.
Figure 6:
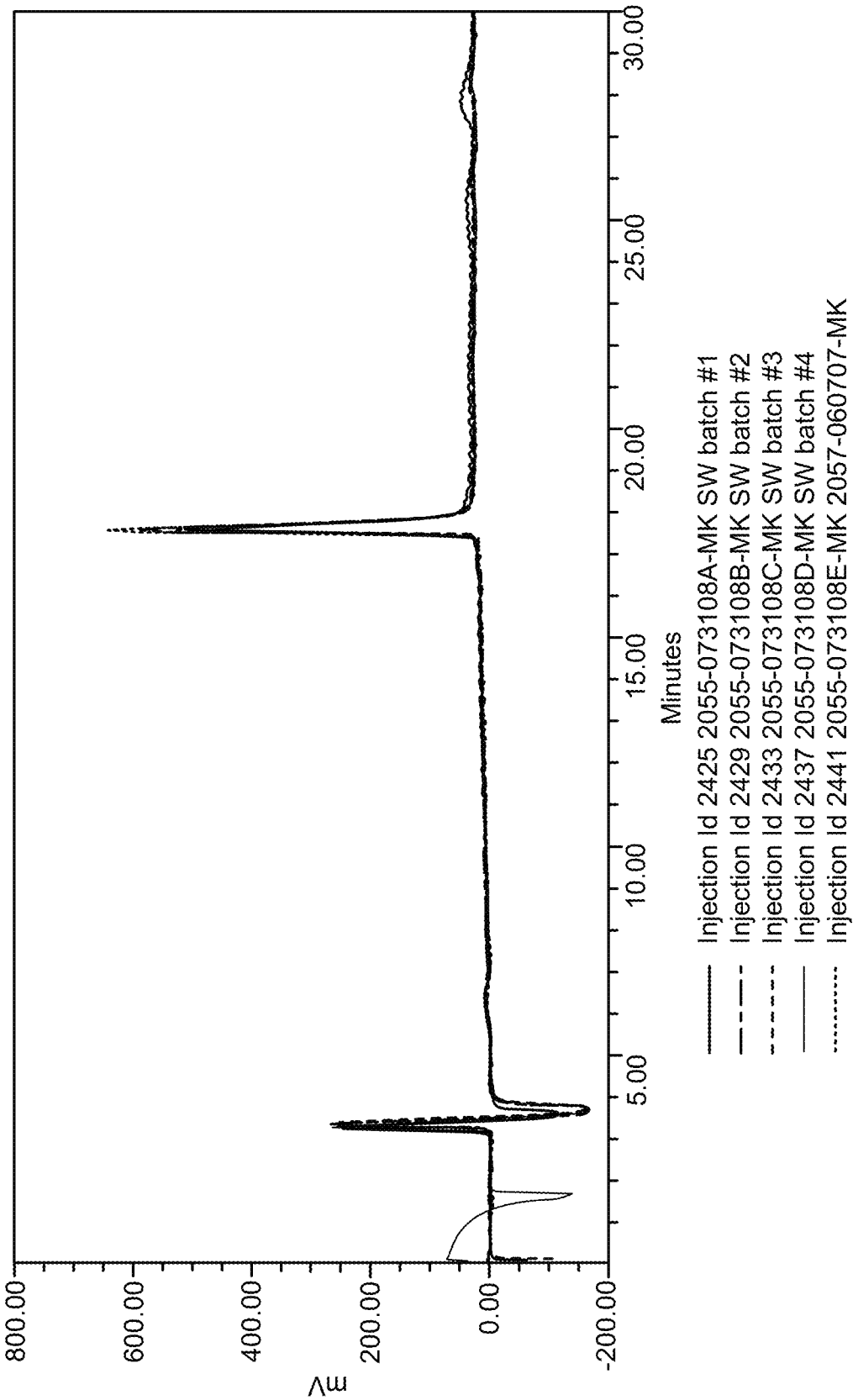
FIG. 6 shows HPLC of non-cleavable SP-SAP on a C4 column.

The non-cleavable conjugate was not susceptible to steady-state disulfide exchange (FIG. 3), and was not reduced by reducing agents such as beta-mercaptoethanol (FIG. 4). By all measurements the non-cleavable SP-SAP was a homogenous protein containing both the SP targeting moiety and the saporin toxin moiety, as demonstrated by C4 HPLC (FIG. 5, FIG. 6). Western blotting of the cleavable SP-SAP conjugate (FIG. 7, FIG. 8) and the non-cleavable conjugate (FIG. 9, FIG. 10) demonstrated that there was no steady-state disulfide exchange occurring in the non-cleavable conjugate. The in vitro cytotoxic activity of the non-cleavable SP-SAP was identical to that of the SPDP-linked cleavable conjugate (FIG. 9).

FIG. 3: Coomassie stained NuPage gel of SP-SAP conjugated with a MPA linker. There is no free $cys^{-1}$-SAP present in either the PBS or borate buffer stored conjugate. The high molecular weight material is due to gel artifacts present when electrophoresing a high isoelectric point protein such as saporin.

FIG. 4: Coomassie stained NuPage gel of SP-SAP conjugated with a maleimide linker compared to SP-SAP with a disulfide linker after treatment with 105 Bis-Tris with 2-Mercaptoethanol.

FIG. 5: Chromatogram of SP-SAP conjugates run over a C4 column in HPLC. Both lots of SP-SAP analyzed were conjugated with SPDP linkers. The main peak is SP-SAP; the secondary peak is dimerized $cys^{-1}$-SAP. The conjugates were run in a mobile phase of 20% acetonitrile/0.1% trifluoroacetic acid, with a 10-90% gradient of 80% acetonitrile/0.1% trifluoroacetic acid.

FIG. 6: Chromatogram of SP-SAP conjugates run over a C4 column in HPLC. These 5 separate batches of SP-SAP were all made using a MPA linker. There is only one peak, indicating that no free $cys^{-1}$-SAP is present. The same run conditions were used as in FIG. 5.

Figure 7:
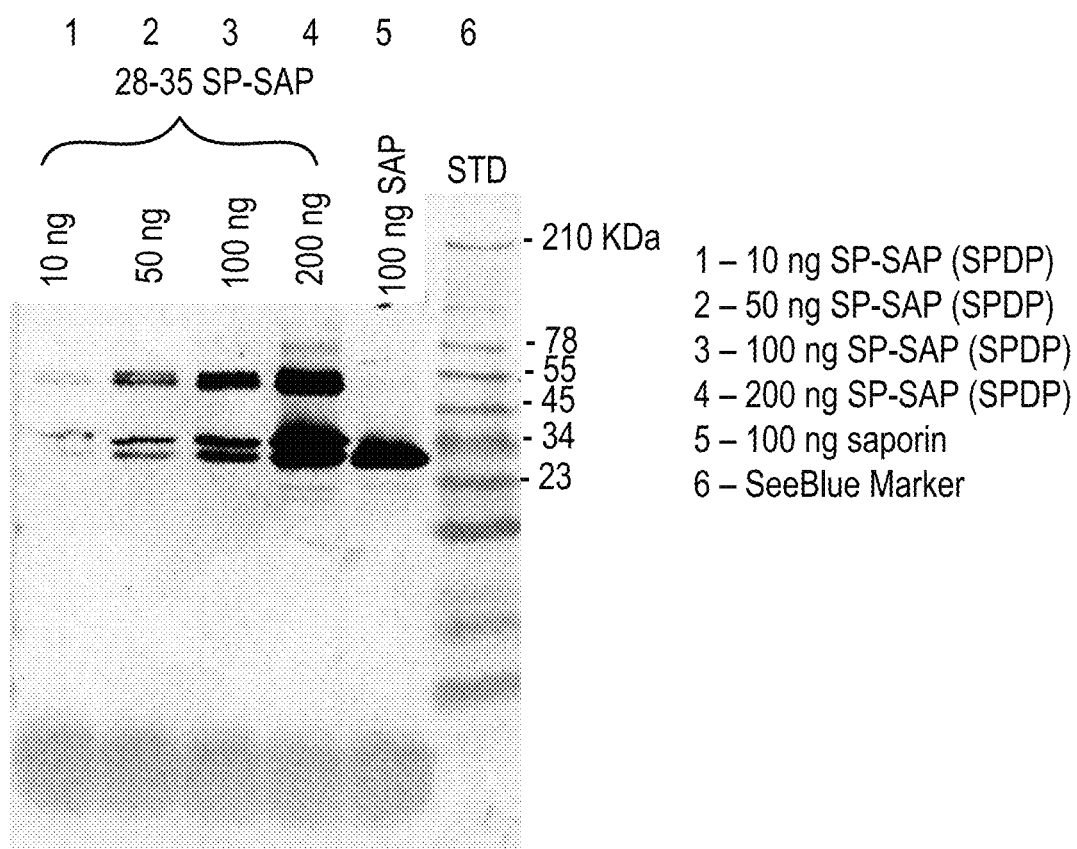
FIG. 7 shows a western blot of cleavable SP-SAP using anti-Saporin.

FIG. 7: Western blot of SP-SAP conjugate made with a SPDP linker. After running the proteins on a NuPage gel, the proteins were transferred to PVDF membrane and incubated with anti-saporin. The 3 visible bands, from top to bottom, are; dimerized $cys^{-1}$-SAP, SP-SAP, and free $cys^{-1}$-SAP.

Figure 8:
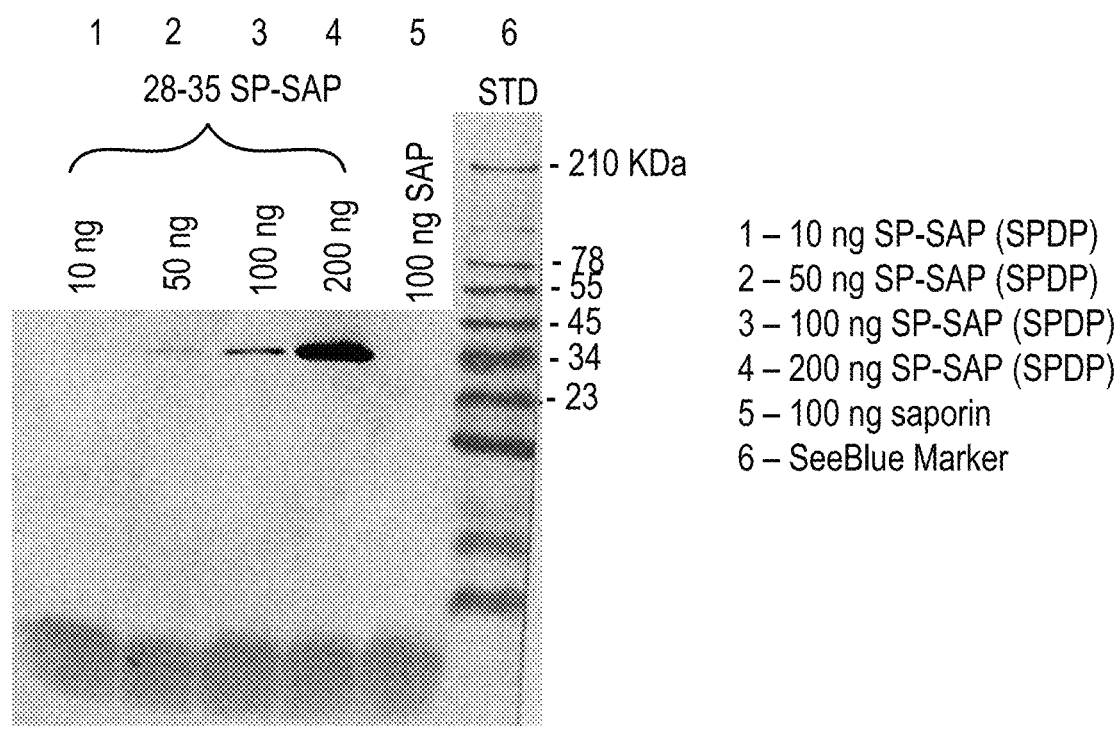
FIG. 8 shows a western blot of cleavable SP-SAP using anti-SP.
Figure 9:
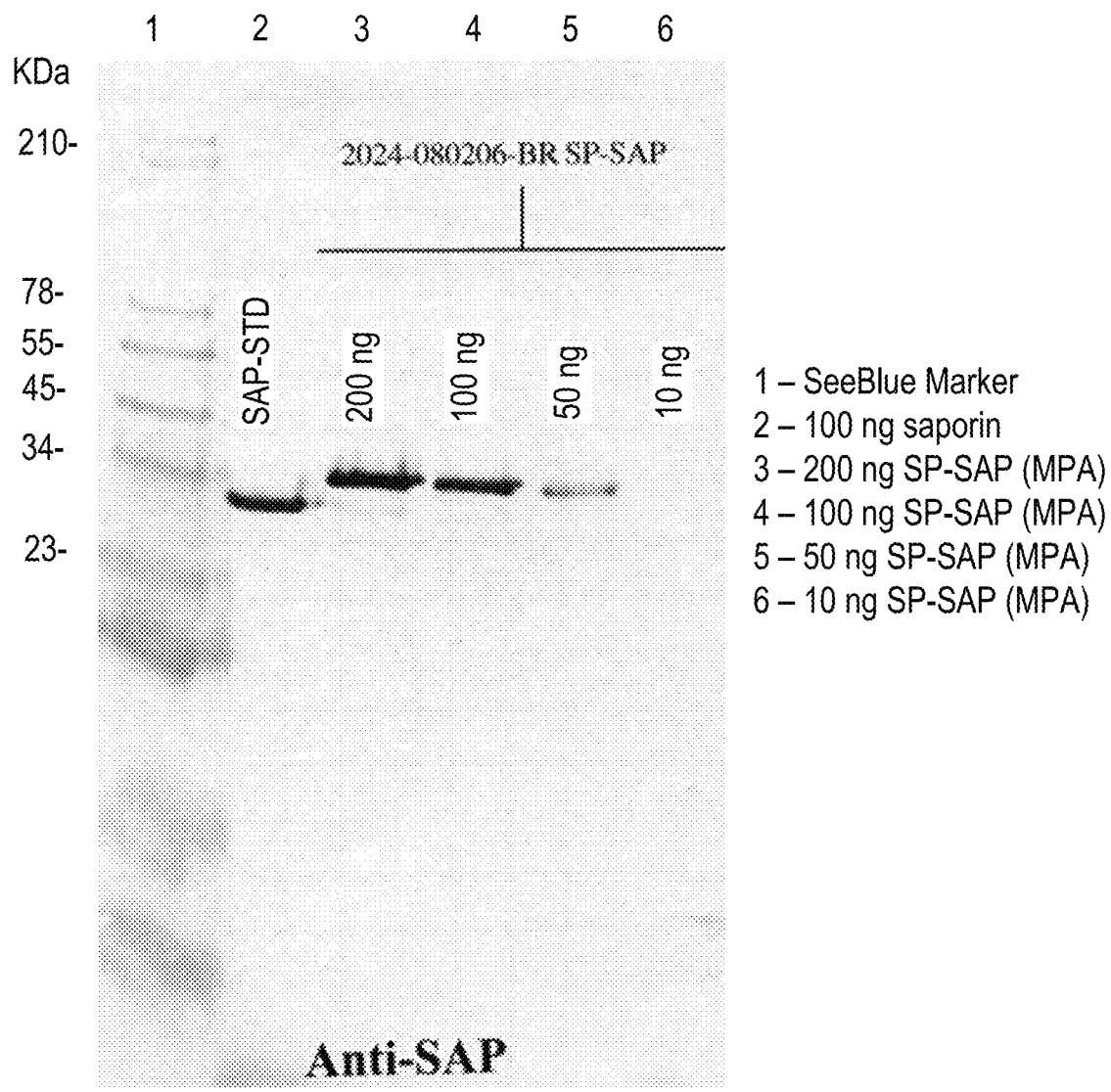
FIG. 9 shows a western blot of non-cleavable SP-SAP using anti-Saporin.

FIG. 8: Western blot of SP-SAP conjugate made with a SPDP linker. After running the proteins on a NuPage gel, the proteins were transferred to PVDF membrane and incubated with anti-SP. This blot is identical to the one in FIG. 7, other than having been probed with an anti-SP antibody instead of an anti-saporin antibody. Substance P is only present on one of the bands visible in FIG. 7.

FIG. 9: Western blot of SP-SAP conjugate made with a MPA linker. After running the proteins on a NuPage gel, the proteins were transferred to PVDF membrane and incubated with anti-saporin. Only one band is visible on this blot, indicating that there is no free $cys^{-1}$-SAP or dimerized $cys^{-1}$-SAP present. There is no disulfide exchange occurring with this conjugate.

Figure 10:
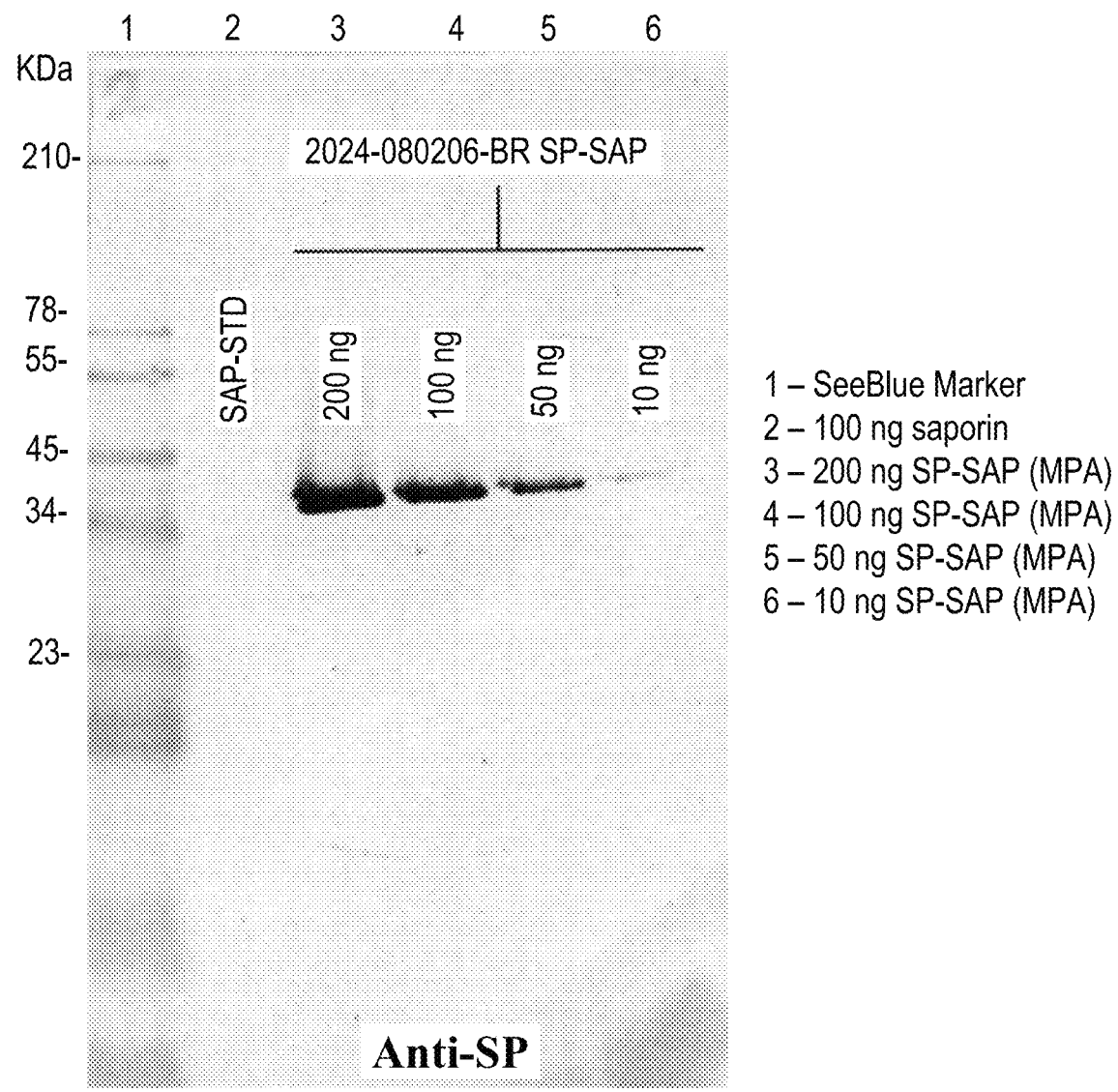
FIG. 10 shows a western blot of non-cleavable SP-SAP using anti-SP.

FIG. 10: Western blot of SP-SAP conjugate made with a MPA linker. After running the proteins on a NuPage gel, the proteins were transferred to PVDF membrane and incubated with anti-SP. Only one band is visible on this blot, and it is the same size as the band visible on the western blot from FIG. 8.

Figure 11:
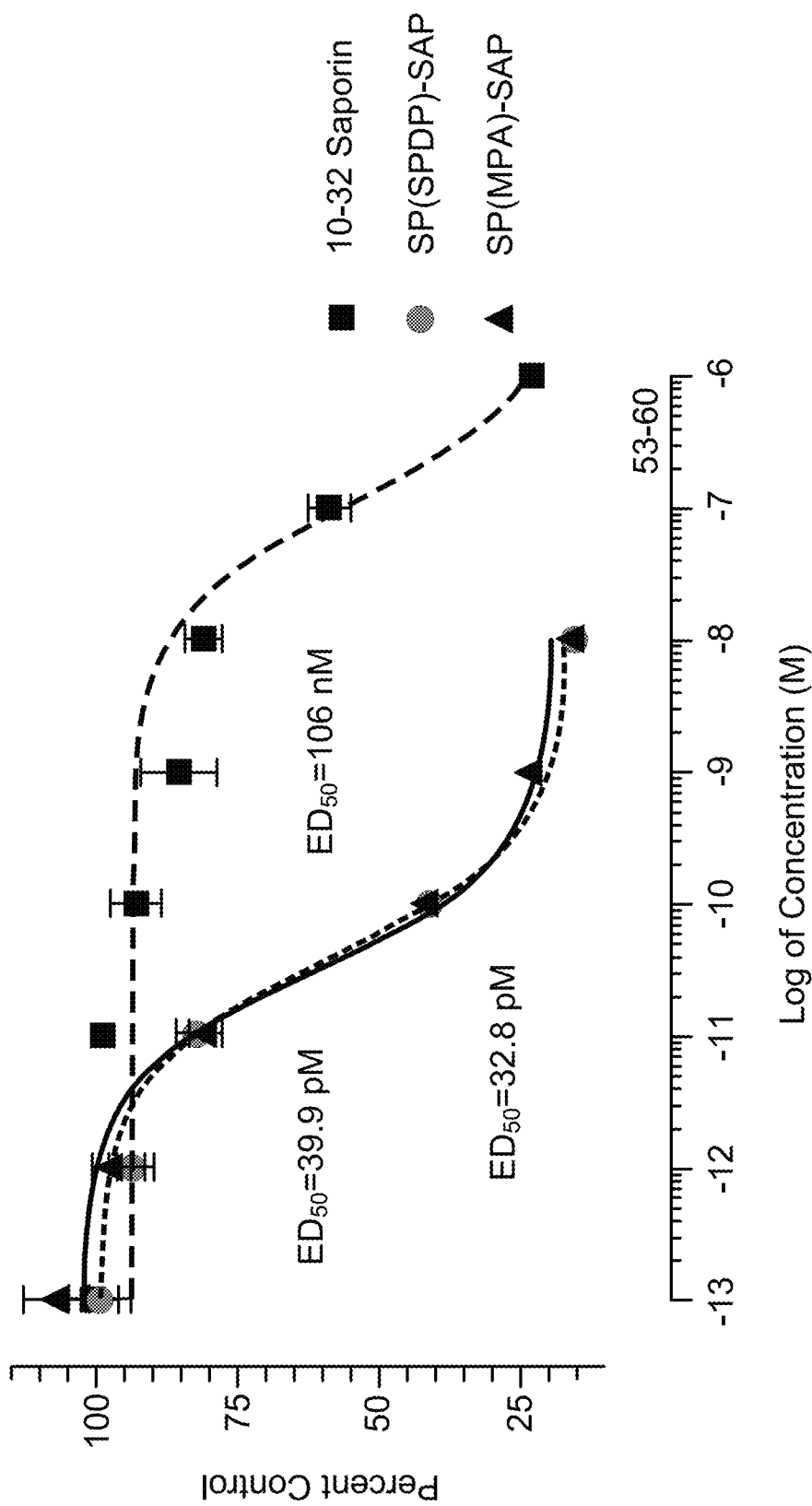
FIG. 11 shows the results of a cytotoxicity assay using cleavable and non-cleavable SP-SAP.

FIG. 11: Cytotoxicity assay comparing SP-SAP conjugated using a SPDP linker to SP-SAP conjugated using a MPA linker. KNRK cells transfected with the NK-1R were incubated in a 96-well plate, and conjugate or saporin control was added to the wells. The $EC_{50}$'s of the two SP-SAP conjugates are virtually identical, indicating that the non-cleavable conjugate maintains full activity.

The synthesis of a non-cleavable substance P conjugate is not straightforward. The carboxy terminus of this peptide is necessary for binding to the NK-1R. The invention describes an N-terminal extension for substance P that contains a maleimidopropionic acid group available for conjugation. The modification allows for the construction of a non-cleavable conjugate maintaining NK-1R-binding activity with the addition of a cell-modifying molecule that will kill or temporarily alter the target cell. This conjugate will bind the NK-1R and be internalized, giving the modifying molecule access to the neuronal cytosol.

The invention described here resolves a serious problem in the synthesis of a disulfide-linked conjugate used as a pharmaceutical agent. After a period of time, particularly at high concentration (>250 µg per mL), the original desired linkage, a disulfide bond connecting the peptidic moiety with the protein moiety will exchange with other disulfide linkages. In the case of the conjugate between a peptide and a protein, new populations will appear after purification of the peptide-protein conjugate. The following possibilities will occur:

1) A peptide-peptide conjugate, a molecule with only peptidic activity, but a competitive binding inhibitor of the peptide-protein moiety.

2) A "new" peptide-protein conjugate, a change with no apparent effect.
3) A peptide-"new" protein conjugate, a change with no apparent effect.
4) A protein-protein conjugate, a change that creates an untargeted molecule with only the protein's activity retained.

Disulfide exchange results in loss of purity and homogeneity of the desired conjugate product, despite extensive purification. It creates new, unwanted, conjugates with undesirable properties. This invention's purpose is to prevent that from happening and the data in the Figures demonstrate this purpose is achieved with this invention.

Characterization of the non-cleavable SP-SAP conjugate was done by cytotoxicity assay (FIG. 11), BCA protein assay, HPLC (FIG. 6), western blotting (FIG. 9, FIG. 10), inhibition assay, endotoxin assay, and coomassie stained SDS-PAGE (FIG. 3).

REFERENCES

1. Thorpe, P. E., et al., *Toxicity of diphtheria toxin for lymphoblastoid cells is increased by conjugation to anti-lymphocytic globulin.* Nature, 1978. 271(5647): p. 752-5.
2. Vitetta, E. S., et al., *Phase I immunotoxin trial in patients with B-cell lymphoma.* Cancer Res, 1991. 51(15): p. 4052-8.
3. Amlot, P. L., et al., *A phase I study of an anti-CD22-deglycosylated ricin A chain immunotoxin in the treatment of B-cell lymphomas resistant to conventional therapy.* Blood, 1993. 82(9): p. 2624-33.
4. Herrera, L., et al., *A phase 1 study of Combotox in pediatric patients with refractory B-lineage acute lymphoblastic leukemia.* J Pediatr Hematol Oncol, 2009. 31(12): p. 936-41.
5. Frankel, A. E., et al., *Anti-CD3 recombinant diphtheria immunotoxin therapy of cutaneous T cell lymphoma.* Curr Drug Targets, 2009. 10(2): p. 104-9.
6. Falini, B., et al., *Response of refractory Hodgkin's disease to monoclonal anti-CD30 immunotoxin.* Lancet, 1992. 339(8803): p. 1195-6.
7. Lappi, D. A., A. Martineau D Fau-Baird, and A. Baird, *Biological and chemical characterization of basic FGF-saporin mitotoxin.* 1989(0006-291X (Print)).
8. Behar-Cohen, F. F., et al., *In vivo inhibition of lens regrowth by fibroblast growth factor 2-saporin.* Invest Ophthalmol Vis Sci, 1995. 36(12): p. 2434-48.
9. Wild, R., et al., *VEGF-DT385 toxin conjugate inhibits mammary adenocarcinoma development in a transgenic mouse model of spontaneous tumorigenesis.* Breast Cancer Res Treat, 2004. 85(2): p. 161-71.
10. Weaver, M. and D. W. Laske, *Transferrin receptor ligand-targeted toxin conjugate (Tf-CRM107) for therapy of malignant gliomas.* J Neurooncol, 2003. 65(1): p. 3-13.
11. Katayama, D. S., M. Cornell Manning, and P. Jarosz, *Solution behavior of a novel biopharmaceutical drug candidate: a gonadotropin-toxin conjugate.* Drug Dev Ind Pharm, 2006. 32(10): p. 1175-84.
12. van de Pavert, S. A., et al., *Effects of vasopressin and elimination of corticotropin-releasing hormone-target cells on pro-opiomelanocortin mRNA levels and adrenocorticotropin secretion in ovine anterior pituitary cells.* J Endocrinol, 1997. 154(1): p. 139-47.
13. Lambert, J. M., et al., *Purified immunotoxins that are reactive with human lymphoid cells. Monoclonal antibodies conjugated to the ribosome-inactivating proteins gelonin and the pokeweed antiviral proteins.* J Biol Chem, 1985. 260(22): p. 12035-41.
14. Masuho, Y., et al., *Importance of the antigen-binding valency and the nature of the cross-linking bond in ricin A-chain conjugates with antibody.* J Biochem, 1982. 91(5): p. 1583-91.
15. Stirpe, F., *Ribosome-inactivating proteins: from toxins to useful proteins.* Toxicon, 2013. 67: p. 12-6.
16. Lyu, M. A., et al., *The rGel/BLyS fusion toxin inhibits diffuse large 8-cell lymphoma growth in vitro and in vivo.* Neoplasia, 2010. 12(5): p. 366-75.
17. Polito, L., et al., *Immunotoxins and other conjugates containing saporin-s6 for cancer therapy.* Toxins (Basel), 2011. 3(6): p. 697-720.
18. Schnell, R., et al., *Clinical evaluation of ricin A-chain immunotoxins in patients with Hodgkin's lymphoma.* Ann Oncol, 2003. 14(5): p. 729-36.
19. Mantyh, P. W., et al., *Inhibition of hyperalgesia by ablation of lamina I spinal neurons expressing the substance P receptor.* Science, 1997. 278(5336): p. 275-9.
20. Bonham, A. C., *Neurotransmitters in the CNS control of breathing.* Respir Physiol, 1995. 101(3): p. 219-30.
21. Ebner, K. and N. Singewald, *The role of substance P in stress and anxiety responses.* Amino Acids, 2006. 31(3): p. 251-72.
22. Huston, J. P., et al., *Sequence-specific effects of neurokinin substance P on memory, reinforcement, and brain dopamine activity.* Psychopharmacology (Berl), 1993. 112(2-3): p. 147-62.
23. Seybold, V. S., *The role of peptides in central sensitization.* Handb Exp Pharmacol, 2009 (194): p. 451-91.
24. Basbaum, A. I., *Spinal mechanisms of acute and persistent pain.* Reg Anesth Pain Med, 1999. 24(1): p. 59-67.
25. Matsumura, H., et al., *Characterization of the hyperalgesic effect induced by intrathecal injection of substance P.* Neuropharmacology, 1985. 24(5): p. 421-6.
26. Almay, B. G., et al., *Substance P in CSF of patients with chronic pain syndromes.* Pain, 1988. 33(1): p. 3-9.
27. Cesaro, P. and H. Ollat, *Pain and its treatments.* Eur Neurol, 1997. 38(3): p. 209-15.
28. Willis, W. D., *Role of neurotransmitters in sensitization of pain responses.* Ann N Y Acad Sci, 2001. 933: p. 142-56.
29. Lappi, D.A.D.M., CA), Wiley, Ronald G. (Brentwood, Tenn.), *Substance P-Saporin (SP-SAP) conjugates and methods of use thereof.* 2000, Advanced Targeting Systems, Inc. (San Diego, Calif.): United States.
30. Wiley, R. G., R. H. t. Kline, and C. J. Vierck, Jr., *Anti-nociceptive effects of selectively destroying substance P receptor-expressing dorsal horn neurons using [Sar9,Met (O2)11]-substance P-saporin: behavioral and anatomical analyses.* Neuroscience, 2007. 146(3): p. 1333-45.
31. Weisshaar, C. L. and B. A. Winkelstein, *Ablating spinal NK1-bearing neurons eliminates the development of pain and reduces spinal neuronal hyperexcitability and inflammation from mechanical joint injury in the rat.* J Pain, 2014. 15(4): p. 378-86.
32. Martin, J. L. and R. S. Sloviter, *Focal inhibitory interneuron loss and principal cell hyperexcitability in the rat hippocampus after microinjection of a neurotoxic conjugate of saporin and a peptidase-resistant analog of Substance P.* J Comp Neurol, 2001. 436(2): p. 127-52.
33. Meini, S., et al., *Tachykinin control of ferret airways: mucus secretion, bronchoconstriction and receptor mapping.* Neuropeptides, 1993. 24(2): p. 81-9.

34. Tousignant, C., et al., *Comparison of binding assay and biological activity on a NK-1 system with new selective agonists.* Neuropeptides, 1989. 14(4): p. 275-83.
35. Sakurada, T., et al., *Behavioral activation of neurokinin-1 agonists in relation to enzymatic degradation in the spinal cord.* J Pharm Sci, 1994. 83(1): p. 2-4.
36. Robertus, J. and M. Monzingo, *Ribosome-inactivating Proteins: Ricin and Related Proteins.* Wiley Blackwell, 2014.
37. Nichols, M. L., et al., *Transmission of chronic nociception by spinal neurons expressing the substance P receptor.* Science, 1999. 286(5444): p. 1558-61.
38. Brown, D. C. and K. Agnello, *Intrathecal substance P-saporin in the dog: efficacy in bone cancer pain.* Anesthesiology, 2013. 119(5): p. 1178-85.
39. Akiyama, T., et al., *A central role for spinal dorsal horn neurons that express neurokinin-1 receptors in chronic itch.* Pain, 2015.
40. Woolf, C. J., *Central sensitization: implications for the diagnosis and treatment of pain.* Pain, 2011. 152(3 Suppl): p. S2-15.
41. Choi, J. I., F. J. Koehrn, and L. S. Sorkin, *Carrageenan induced phosphorylation of Akt is dependent on neurokinin-1 expressing neurons in the superficial dorsal horn.* Mol Pain, 2012. 8: p. 4.
42. Khasabov, S. G., et al., *Spinal neurons that possess the substance P receptor are required for the development of central sensitization.* J Neurosci, 2002. 22(20): p. 9086-98.
43. Suzuki, R., et al., *Superficial NK1-expressing neurons control spinal excitability through activation of descending pathways.* Nat Neurosci, 2002. 5(12): p. 1319-26.
44. Meeus, M. and J. Nijs, *Central sensitization: a biopsychosocial explanation for chronic widespread pain in patients with fibromyalgia and chronic fatigue syndrome.* Clin Rheumatol, 2007. 26(4): p. 465-73.
45. Moeller-Bertram, T., et al., *Evidence for acute central sensitization to prolonged experimental pain in posttraumatic stress disorder.* Pain Med, 2014. 15(5): p. 762-71.
46. Pergolizzi, J. V., C. Gharibo, and K. Y. Ho, *Treatment Considerations for Cancer Pain: A Global Perspective.* Pain Pract, 2014.
47. Lamanna, C., O. E. McElroy, and H. W. Eklund, *The Purification and Crystallization of Clostridium botulinum Type A Toxin.* Science, 1946. 103(2681): p. 613-4.
48. Blasi, J., et al., *Botulinum neurotoxin A selectively cleaves the synaptic protein SNAP-25.* Nature, 1993. 365(6442): p. 160-3.
49. Montecucco, C. and G. Schiavo, *Tetanus and botulism neurotoxins: a new group of zinc proteases.* Trends Biochem Sci, 1993. 18(9): p. 324-7.
50. Foran, P. G., et al., *Evaluation of the therapeutic usefulness of botulinum neurotoxin B, C1, E, and F compared with the long lasting type A. Basis for distinct durations of inhibition of exocytosis in central neurons.* J Biol Chem, 2003. 278(2): p. 1363-71.
51. Ranoux, D., et al., *Botulinum toxin type A induces direct analgesic effects in chronic neuropathic pain.* Ann Neurol, 2008. 64(3): p. 274-83.
52. Brin, M. F., et al., *Safety and efficacy of NeuroBloc (botulinum toxin type B) in type A-resistant cervical dystonia.* Neurology, 1999. 53(7): p. 1431-8.
53. Nagy, P., *Kinetics and mechanisms of thiol-disulfide exchange covering direct substitution and thiol oxidation-mediated pathways.* Antioxid Redox Signal, 2013. 18(13): p. 1623-41.
54. Cava, M., et al., *N-Phenylmaleimide.* Organic Syntheses, 1961. 41(93).
55. Rajashekhar, B. and E. T. Kaiser, *Design of biologically active peptides with non-peptidic structural elements. Biological and physical properties of a synthetic analogue of beta-endorphin with unnatural amino acids in the region 6-12.* J Biol Chem, 1986. 261(29): p. 13617-23.

The invention claimed is:

1. A non-cleavable conjugate comprising:
   a) a substance P analog selected from the group consisting of Maleimidopropionic acid (MPA)GGGGG-GRPKPQQFF SarLMet(O$_2$)-amide (SEQ ID No.:1) and Maleimidopropionic acid (MPA)GGGGG-GRPKPQQFFGLM-amide (SEQ ID No.:2); and
   b) a saporin, an analog or a fragment thereof, that is taken inside a cell to kill alter the cell, wherein said saporin, analog or fragment thereof, is linked to said substance P analog via MPA; and
   wherein said saporin, analog or fragment thereof maintains its cell altering activity.

2. The non-cleavable conjugate of claim 1, wherein the saporin is a ribosome-inactivating protein.

3. A pharmaceutical composition comprising a therapeutically effective amount of the non-cleavable conjugate of claim 1 and a pharmaceutically acceptable carrier.

4. A method for treating the symptoms of itch in a subject which comprises administering to the subject an effective amount of the pharmaceutical composition of claim 3.

* * * * *

SEQUENCE LISTING

```
<160> NUMBER OF SEQ ID NOS: 3

<210> SEQ ID NO 1
<211> LENGTH: 17
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Maleimidopropionic acid
<220> FEATURE:
<221> NAME/KEY: MOD_RES
<222> LOCATION: (15)..(15)
<223> OTHER INFORMATION: Sarcosine
<220> FEATURE:
<221> NAME/KEY: MOD_RES
<222> LOCATION: (17)..(17)
<223> OTHER INFORMATION: Oxidized methionine

<400> SEQUENCE: 1

Xaa Gly Gly Gly Gly Gly Gly Lys Pro Lys Gln Gln Phe Phe Xaa Leu
1               5                   10                  15

Met

<210> SEQ ID NO 2
<211> LENGTH: 18
<212> TYPE: PRT
<213> ORGANISM: Homo sapiens
```

```
<220> FEATURE:
<221> NAME/KEY: MOD_RES
<222> LOCATION: (1)..(1)
<223> OTHER INFORMATION: Maleimidopropionic acid

<400> SEQUENCE: 2

Xaa Gly Gly Gly Gly Gly Gly Arg Pro Lys Pro Gln Gln Phe Phe Gly
1               5                   10                  15

Leu Met

<210> SEQ ID NO 3
<211> LENGTH: 18
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Maleimidopropionic acid
<220> FEATURE:
<221> NAME/KEY: MOD_RES
<222> LOCATION: (16)..(16)
<223> OTHER INFORMATION: Sarcosine
<220> FEATURE:
<221> NAME/KEY: MOD_RES
<222> LOCATION: (18)..(18)
<223> OTHER INFORMATION: Oxidized methionine

<400> SEQUENCE: 3

Xaa Gly Gly Gly Gly Gly Gly Arg Pro Lys Pro Gln Gln Phe Phe Xaa
1               5                   10                  15

Leu Met
```